US009339323B2

(12) United States Patent
Eder et al.

(10) Patent No.: US 9,339,323 B2
(45) Date of Patent: *May 17, 2016

(54) ELECTROCAUTERY METHOD AND APPARATUS

(75) Inventors: Joseph Charles Eder, Los Altos Hills, CA (US); Benjamin Theodore Nordell, II, San Mateo, CA (US); Peter Seth Edelstein, Menlo Park, CA (US); Camran Nezhat, Woodside, CA (US); Mark Kane, San Jose, CA (US); Erik Walberg, Redwood City, CA (US)

(73) Assignee: Aesculap AG (DE)

( * ) Notice: Subject to any disclaimer, the term of this patent is extended or adjusted under 35 U.S.C. 154(b) by 440 days.

This patent is subject to a terminal disclaimer.

(21) Appl. No.: 12/121,734

(22) Filed: May 15, 2008

(65) Prior Publication Data

US 2008/0221565 A1    Sep. 11, 2008

Related U.S. Application Data

(63) Continuation-in-part of application No. 11/671,891, filed on Feb. 6, 2007, now Pat. No. 8,696,662, which is a continuation-in-part of application No. 11/382,635, filed on May 10, 2006, now Pat. No. 7,862,565, and a (Continued)

(51) Int. Cl.
*A61B 18/12* (2006.01)
*A61B 18/14* (2006.01)

(Continued)

(52) U.S. Cl.
CPC ......... *A61B 18/1206* (2013.01); *A61B 18/1442* (2013.01); *A61B 2017/0088* (2013.01);

(Continued)

(58) Field of Classification Search
CPC ........... A61B 2019/465; A61B 5/6843; A61B 5/6885; A61B 5/6886; A61B 2017/00026; A61B 2018/00875; A61B 5/053; A61B 5/0531; A61B 2018/00732; A61B 2018/00755
USPC ..................................................... 606/34, 38
See application file for complete search history.

(56) References Cited

U.S. PATENT DOCUMENTS 3,356,408 A    12/1967  Stutz
3,527,224 A     9/1970  Rabinowitz
(Continued)

FOREIGN PATENT DOCUMENTS

CA    2061215     2/1992
CN    1250360 A   4/2000
(Continued)

OTHER PUBLICATIONS

Abu-Rustum, NR, et al.; *Transperitoneal Laparoscopic Pelvic and Para-Aortic Lymph Node Dissection Using The Argon-Beam Coagulator and Monopolar Instruments: An 8-Year Study and Description of Technique*; Jun. 2003; Gynecol Oncol. 89 (3): 504-13; Memorial Sloan-Kettering Cancer Center, 1275 York Avenue, New York, NY 10021, USA. gynbreast@mskcc.org.

(Continued)

*Primary Examiner* — Jaymi Della
(74) *Attorney, Agent, or Firm* — RatnerPrestia

(57) ABSTRACT

An electrode structure and a mechanism for automated or user-selected operation or compensation of the electrodes, for example to determine tissue coverage and/or prevent arcing between bottom electrodes during electrocautery is disclosed.

24 Claims, 8 Drawing Sheets

Related U.S. Application Data continuation-in-part of application No. 11/371,988, filed on Mar. 8, 2006, now Pat. No. 7,803,156.

(60) Provisional application No. 60/725,720, filed on Oct. 11, 2005, provisional application No. 60/680,937, filed on May 12, 2005.

(51) Int. Cl.
*A61B 17/00* (2006.01)
*A61B 18/00* (2006.01)

(52) U.S. Cl.
CPC ............... *A61B2018/0063* (2013.01); *A61B 2018/00107* (2013.01); *A61B 2018/00136* (2013.01); *A61B 2018/00148* (2013.01); *A61B 2018/00505* (2013.01); *A61B 2018/00595* (2013.01); *A61B 2018/00648* (2013.01); *A61B 2018/00678* (2013.01); *A61B 2018/00702* (2013.01); *A61B 2018/00779* (2013.01); *A61B 2018/00791* (2013.01); *A61B 2018/00827* (2013.01); *A61B 2018/00869* (2013.01); *A61B 2018/00875* (2013.01); *A61B 2018/00892* (2013.01); *A61B 2018/1273* (2013.01)

(56) References Cited

U.S. PATENT DOCUMENTS

| | | |
|---|---|---|
| 3,709,215 A | 1/1973 | Richmond |
| 3,742,955 A | 7/1973 | Battista et al. |
| 3,845,771 A | 11/1974 | Vise |
| 3,920,021 A | 11/1975 | Hiltebrandt |
| 3,970,088 A | 7/1976 | Morrison |
| 4,018,230 A | 4/1977 | Ochiai et al. |
| 4,041,952 A | 8/1977 | Morrison et al. |
| 4,072,153 A | 2/1978 | Swartz |
| 4,094,320 A | 6/1978 | Newton et al. |
| 4,200,104 A | 4/1980 | Harris |
| 4,231,372 A | 11/1980 | Newton |
| 4,492,231 A | 1/1985 | Auth |
| 4,532,924 A | 8/1985 | Auth et al. |
| 4,590,934 A | 5/1986 | Malis et al. |
| 4,671,274 A | 6/1987 | Sorochenko |
| 4,867,649 A | 9/1989 | Kawashima |
| 4,972,846 A | 11/1990 | Owens et al. |
| 4,976,717 A | 12/1990 | Boyle |
| 4,979,948 A | 12/1990 | Geddes et al. |
| 4,998,527 A | 3/1991 | Meyer |
| 5,037,379 A | 8/1991 | Clayman et al. |
| 5,041,101 A | 8/1991 | Seder et al. |
| 5,059,782 A | 10/1991 | Fukuyama |
| 5,078,736 A | 1/1992 | Behl |
| 5,108,408 A | 4/1992 | Lally |
| 5,133,713 A | 7/1992 | Huang et al. |
| 5,151,102 A | 9/1992 | Kamiyama |
| 5,156,613 A | 10/1992 | Sawyer |
| 5,178,618 A | 1/1993 | Kandarpa |
| 5,190,541 A | 3/1993 | Abele et al. |
| 5,207,691 A | 5/1993 | Nardella |
| 5,217,030 A | 6/1993 | Yoon |
| 5,234,425 A | 8/1993 | Fogarty et al. |
| 5,250,074 A | 10/1993 | Wilk et al. |
| 5,267,998 A | 12/1993 | Hagen |
| 5,269,780 A | 12/1993 | Roos |
| 5,269,782 A | 12/1993 | Sutter |
| 5,273,524 A | 12/1993 | Fox et al. |
| 5,277,201 A | 1/1994 | Stern |
| 5,281,216 A | 1/1994 | Klicek |
| 5,282,799 A | 2/1994 | Rydell |
| 5,290,287 A | 3/1994 | Boebel et al. |
| 5,295,990 A | 3/1994 | Levin |
| 5,300,068 A * | 4/1994 | Rosar et al. ............ 606/34 |
| 5,300,087 A | 4/1994 | Knoepfler |
| 5,312,023 A | 5/1994 | Green et al. |
| 5,324,289 A | 6/1994 | Eggers |
| 5,330,471 A | 7/1994 | Eggers |
| 5,330,502 A | 7/1994 | Hassler et al. |
| 5,336,229 A | 8/1994 | Noda |
| 5,336,237 A | 8/1994 | Chin et al. |
| 5,341,807 A | 8/1994 | Nardella |
| 5,342,381 A | 8/1994 | Tidemand |
| 5,352,223 A | 10/1994 | McBrayer et al. |
| 5,352,235 A | 10/1994 | Koros et al. |
| 5,354,336 A | 10/1994 | Kelman et al. |
| 5,356,408 A | 10/1994 | Rydell |
| 5,374,277 A | 12/1994 | Hassler |
| 5,377,415 A | 1/1995 | Gibson |
| 5,391,166 A | 2/1995 | Eggers |
| 5,395,369 A | 3/1995 | McBrayer et al. |
| 5,396,900 A | 3/1995 | Slater et al. |
| 5,397,320 A | 3/1995 | Essig |
| 5,403,312 A | 4/1995 | Yates et al. |
| 5,417,687 A | 5/1995 | Nardella et al. |
| 5,423,809 A | 6/1995 | Klicek |
| 5,423,814 A | 6/1995 | Zhu et al. |
| 5,431,676 A | 7/1995 | Dubrul |
| 5,438,302 A * | 8/1995 | Goble ............ 331/167 |
| 5,443,463 A | 8/1995 | Stern et al. |
| 5,443,470 A | 8/1995 | Stern et al. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,462,546 A | 10/1995 | Rydell |
| 5,472,442 A | 12/1995 | Klicek |
| 5,480,399 A | 1/1996 | Hebborn |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,520,698 A | 5/1996 | Koh |
| 5,531,744 A | 7/1996 | Nardella et al. |
| 5,540,684 A | 7/1996 | Hassler, Jr. |
| 5,540,685 A | 7/1996 | Parins et al. |
| 5,542,945 A | 8/1996 | Fritzsch |
| 5,549,606 A | 8/1996 | McBrayer et al. |
| 5,549,637 A | 8/1996 | Crainich |
| 5,556,397 A | 9/1996 | Long et al. |
| 5,558,100 A | 9/1996 | Cox |
| 5,558,671 A | 9/1996 | Yates |
| 5,562,700 A | 10/1996 | Huitema et al. |
| 5,562,701 A | 10/1996 | Huitema et al. |
| 5,562,702 A | 10/1996 | Huitema et al. |
| 5,562,720 A | 10/1996 | Stern et al. |
| 5,564,615 A | 10/1996 | Bishop et al. |
| 5,569,243 A | 10/1996 | Kortenbach |
| 5,571,100 A | 11/1996 | Goble et al. |
| 5,573,535 A | 11/1996 | Viklund |
| 5,578,052 A | 11/1996 | Koros et al. |
| 5,599,350 A | 2/1997 | Schulze et al. |
| 5,601,224 A | 2/1997 | Bishop et al. |
| 5,603,700 A | 2/1997 | Daneshvar |
| 5,603,711 A | 2/1997 | Parins et al. |
| 5,611,803 A | 3/1997 | Heaven |
| 5,624,452 A | 4/1997 | Yates |
| 5,637,110 A | 6/1997 | Pennybacker |
| 5,637,111 A | 6/1997 | Sutcu et al. |
| 5,653,692 A | 8/1997 | Masterson et al. |
| 5,658,281 A | 8/1997 | Heard |
| 5,662,662 A | 9/1997 | Bishop et al. |
| 5,662,676 A | 9/1997 | Koninckx |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt et al. |
| 5,673,840 A | 10/1997 | Schulze et al. |
| 5,673,841 A | 10/1997 | Schulze et al. |
| 5,674,184 A | 10/1997 | Hassler, Jr. |
| 5,674,220 A | 10/1997 | Fox et al. |
| 5,675,184 A | 10/1997 | Matsubayashi et al. |

(56) References Cited

U.S. PATENT DOCUMENTS

| | | | |
|---|---|---|---|
| 5,680,982 A | 10/1997 | Schulze et al. | |
| 5,681,282 A | 10/1997 | Eggers et al. | |
| 5,683,385 A | 11/1997 | Kortenbach | |
| 5,683,388 A | 11/1997 | Slater | |
| 5,688,270 A | 11/1997 | Yates et al. | |
| 5,693,051 A | 12/1997 | Schulze et al. | |
| 5,697,949 A | 12/1997 | Giurtino et al. | |
| 5,700,261 A | 12/1997 | Brinkerhoff | |
| 5,702,390 A | 12/1997 | Austin et al. | |
| 5,704,534 A | 1/1998 | Huitema et al. | |
| 5,707,369 A | 1/1998 | Vaitekunas et al. | |
| 5,709,680 A | 1/1998 | Yates et al. | |
| 5,713,896 A | 2/1998 | Nardella et al. | |
| 5,715,832 A | 2/1998 | Koblish et al. | |
| 5,718,703 A | 2/1998 | Chin | |
| 5,720,719 A | 2/1998 | Edwards et al. | |
| 5,728,143 A | 3/1998 | Gough et al. | |
| 5,733,283 A | 3/1998 | Malis et al. | |
| 5,735,289 A | 4/1998 | Pfeffer et al. | |
| 5,735,848 A | 4/1998 | Yates et al. | |
| 5,735,849 A | 4/1998 | Baden et al. | |
| 5,741,285 A | 4/1998 | McBrayer | |
| 5,743,906 A | 4/1998 | Parins et al. | |
| 5,746,750 A | 5/1998 | Prestel et al. | |
| 5,749,895 A | 5/1998 | Sawyer et al. | |
| 5,755,717 A | 5/1998 | Yates et al. | |
| 5,769,849 A | 6/1998 | Eggers | |
| 5,776,130 A | 7/1998 | Buysse et al. | |
| 5,788,662 A | 8/1998 | Antanavich et al. | |
| 5,797,906 A | 8/1998 | Rhum et al. | |
| 5,797,941 A | 8/1998 | Schulze et al. | |
| 5,810,811 A | 9/1998 | Yates et al. | |
| 5,817,091 A | 10/1998 | Nardella et al. | |
| 5,817,092 A | 10/1998 | Behl | |
| 5,823,066 A | 10/1998 | Huitema et al. | |
| 5,833,689 A | 11/1998 | Long | |
| 5,833,690 A | 11/1998 | Yates et al. | |
| 5,836,990 A | 11/1998 | Li | |
| 5,840,077 A | 11/1998 | Rowden et al. | |
| 5,855,576 A | 1/1999 | LeVeen et al. | |
| 5,860,975 A | 1/1999 | Goble et al. | |
| 5,891,142 A | 4/1999 | Eggers et al. | |
| 5,893,835 A | 4/1999 | Witt et al. | |
| 5,893,874 A | 4/1999 | Bourque et al. | |
| 5,931,835 A * | 8/1999 | Mackey | 606/34 |
| 5,931,836 A | 8/1999 | Hatta et al. | |
| 5,954,720 A | 9/1999 | Wilson et al. | |
| 5,976,128 A * | 11/1999 | Schilling et al. | 606/34 |
| 5,979,453 A | 11/1999 | Savage et al. | |
| 5,983,874 A | 11/1999 | Suzuki | |
| 6,003,517 A | 12/1999 | Sheffield et al. | |
| 6,004,319 A | 12/1999 | Goble et al. | |
| 6,030,384 A | 2/2000 | Nezhat | |
| 6,039,735 A | 3/2000 | Greep | |
| 6,050,993 A | 4/2000 | Tu et al. | |
| 6,050,995 A | 4/2000 | Durgin | |
| 6,056,744 A | 5/2000 | Edwards | |
| 6,056,746 A | 5/2000 | Goble et al. | |
| 6,059,766 A | 5/2000 | Greff | |
| 6,059,782 A | 5/2000 | Novak et al. | |
| 6,066,139 A | 5/2000 | Ryan et al. | |
| 6,068,626 A | 5/2000 | Harrington et al. | |
| 6,071,281 A | 6/2000 | Burnside et al. | |
| 6,074,386 A | 6/2000 | Goble et al. | |
| 6,086,586 A | 7/2000 | Hooven | |
| 6,090,106 A | 7/2000 | Goble et al. | |
| 6,093,186 A | 7/2000 | Goble | |
| 6,096,037 A | 8/2000 | Mulier et al. | |
| 6,099,550 A | 8/2000 | Yoon | |
| 6,123,701 A | 9/2000 | Nezhat | |
| H1904 H | 10/2000 | Yates et al. | |
| 6,142,992 A | 11/2000 | Cheng et al. | |
| 6,152,920 A | 11/2000 | Thompson et al. | |
| 6,152,932 A | 11/2000 | Ternstrom | |
| 6,162,220 A | 12/2000 | Nezhat | |
| 6,174,309 B1 | 1/2001 | Wrublewski et al. | |
| 6,179,832 B1 | 1/2001 | Jones et al. | |
| 6,203,541 B1 | 3/2001 | Keppel | |
| 6,203,542 B1 | 3/2001 | Ellsberry et al. | |
| 6,206,877 B1 | 3/2001 | Kese et al. | |
| 6,210,406 B1 * | 4/2001 | Webster | 606/41 |
| 6,212,426 B1 * | 4/2001 | Swanson | 600/510 |
| 6,217,894 B1 | 4/2001 | Sawhney et al. | |
| 6,228,084 B1 | 5/2001 | Kirwan, Jr. | |
| 6,234,178 B1 | 5/2001 | Goble et al. | |
| 6,241,139 B1 | 6/2001 | Milliman et al. | |
| 6,245,069 B1 | 6/2001 | Gminder | |
| 6,254,601 B1 | 7/2001 | Burbank et al. | |
| 6,258,085 B1 | 7/2001 | Eggleston | |
| 6,277,114 B1 | 8/2001 | Bullivant et al. | |
| 6,283,963 B1 | 9/2001 | Regula | |
| 6,287,304 B1 | 9/2001 | Eggers et al. | |
| 6,290,715 B1 | 9/2001 | Sharkey et al. | |
| 6,293,942 B1 | 9/2001 | Goble et al. | |
| 6,293,946 B1 | 9/2001 | Thorne | |
| 6,296,636 B1 | 10/2001 | Cheng et al. | |
| 6,306,134 B1 | 10/2001 | Goble et al. | |
| 6,312,430 B1 | 11/2001 | Wilson et al. | |
| 6,322,494 B1 | 11/2001 | Bullivant et al. | |
| 6,327,505 B1 | 12/2001 | Medhkour et al. | |
| 6,334,861 B1 | 1/2002 | Chandler et al. | |
| 6,350,274 B1 | 2/2002 | Li | |
| 6,361,559 B1 | 3/2002 | Hauser et al. | |
| 6,364,879 B1 | 4/2002 | Chen et al. | |
| 6,371,956 B1 | 4/2002 | Wilson et al. | |
| 6,391,024 B1 | 5/2002 | Sun et al. | |
| 6,391,029 B1 | 5/2002 | Hooven et al. | |
| 6,398,779 B1 | 6/2002 | Buysse et al. | |
| 6,398,781 B1 | 6/2002 | Goble et al. | |
| H2037 H | 7/2002 | Yates et al. | |
| 6,416,509 B1 | 7/2002 | Goble | |
| 6,423,057 B1 | 7/2002 | He | |
| 6,428,550 B1 | 8/2002 | Vargas et al. | |
| 6,436,096 B1 | 8/2002 | Hareyama | |
| 6,440,130 B1 | 8/2002 | Mulier et al. | |
| 6,443,952 B1 | 9/2002 | Mulier et al. | |
| 6,464,702 B2 | 10/2002 | Schulze et al. | |
| 6,485,486 B1 | 11/2002 | Trembly et al. | |
| 6,485,489 B2 | 11/2002 | Teirstein et al. | |
| 6,491,690 B1 | 12/2002 | Goble et al. | |
| 6,494,881 B1 | 12/2002 | Bales et al. | |
| 6,500,176 B1 | 12/2002 | Truckai et al. | |
| 6,514,252 B2 | 2/2003 | Nezhat et al. | |
| 6,517,530 B1 | 2/2003 | Kleven | |
| 6,520,185 B1 | 2/2003 | Bommannan et al. | |
| 6,533,784 B2 | 3/2003 | Truckai et al. | |
| 6,546,933 B1 | 4/2003 | Yoon | |
| 6,554,829 B2 | 4/2003 | Schulze et al. | |
| 6,564,806 B1 | 5/2003 | Fogarty et al. | |
| 6,565,560 B1 | 5/2003 | Goble et al. | |
| 6,565,561 B1 | 5/2003 | Goble et al. | |
| 6,584,360 B2 | 6/2003 | Francischelli | |
| 6,610,060 B2 | 8/2003 | Mulier et al. | |
| 6,610,074 B2 | 8/2003 | Santilli | |
| 6,613,048 B2 | 9/2003 | Mulier et al. | |
| 6,616,654 B2 | 9/2003 | Mollenauer | |
| 6,616,659 B1 | 9/2003 | de la Torre et al. | |
| 6,619,529 B2 | 9/2003 | Green et al. | |
| 6,623,482 B2 | 9/2003 | Pendekanti et al. | |
| 6,626,901 B1 | 9/2003 | Treat et al. | |
| 6,645,198 B1 | 11/2003 | Bommannan et al. | |
| 6,645,201 B1 | 11/2003 | Utley et al. | |
| 6,648,839 B2 | 11/2003 | Manna | |
| 6,652,518 B2 | 11/2003 | Wellman | |
| 6,656,177 B2 | 12/2003 | Truckai et al. | |
| 6,666,859 B1 | 12/2003 | Fleenor et al. | |
| 6,673,085 B1 | 1/2004 | Berg | |
| 6,676,660 B2 | 1/2004 | Wampler et al. | |
| 6,682,526 B1 | 1/2004 | Jones et al. | |
| 6,682,527 B2 | 1/2004 | Strul | |
| 6,695,840 B2 | 2/2004 | Schulze | |
| 6,699,245 B2 | 3/2004 | Dinger et al. | |
| 6,719,754 B2 | 4/2004 | Underwood et al. | |
| 6,722,371 B1 | 4/2004 | Fogarty et al. | |

(56) References Cited

U.S. PATENT DOCUMENTS

| | | |
|---|---|---|
| 6,726,682 B2 | 4/2004 | Harrington et al. |
| 6,736,814 B2 | 5/2004 | Manna et al. |
| 6,743,229 B2 | 6/2004 | Buysse et al. |
| 6,746,488 B1 | 6/2004 | Bales |
| 6,752,154 B2 | 6/2004 | Fogarty et al. |
| 6,752,803 B2 | 6/2004 | Goldman et al. |
| 6,755,827 B2 | 6/2004 | Mulier et al. |
| 6,770,070 B1 | 8/2004 | Balbierz |
| 6,770,072 B1 | 8/2004 | Truckai et al. |
| 6,773,435 B2 | 8/2004 | Schulze et al. |
| 6,776,780 B2 | 8/2004 | Mulier et al. |
| 6,796,981 B2 | 9/2004 | Wham |
| 6,808,525 B2 | 10/2004 | Latterell et al. |
| 6,817,974 B2 | 11/2004 | Cooper et al. |
| 6,821,273 B2 | 11/2004 | Mollenauer |
| 6,837,888 B2 | 1/2005 | Ciarrocca et al. |
| 6,840,938 B1 | 1/2005 | Morley et al. |
| 6,843,789 B2 | 1/2005 | Goble |
| 6,852,108 B2 | 2/2005 | Barry et al. |
| 6,858,028 B2 | 2/2005 | Mulier et al. |
| 6,889,089 B2 | 5/2005 | Behl et al. |
| 6,893,435 B2 | 5/2005 | Goble |
| 6,896,672 B1 | 5/2005 | Eggers et al. |
| 6,896,673 B2 | 5/2005 | Hooven |
| 6,902,536 B2 | 6/2005 | Manna et al. |
| 6,905,506 B2 | 6/2005 | Burbank et al. |
| 6,908,463 B2 | 6/2005 | Treat et al. |
| 6,913,579 B2 | 7/2005 | Truckai et al. |
| 6,918,909 B2 | 7/2005 | Ohyama et al. |
| 6,923,803 B2 | 8/2005 | Goble |
| 6,923,806 B2 | 8/2005 | Hooven et al. |
| 6,926,712 B2 | 8/2005 | Phan |
| 6,929,642 B2 | 8/2005 | Xiao et al. |
| 6,936,048 B2 | 8/2005 | Hurst |
| 6,939,346 B2 | 9/2005 | Kannenberg et al. |
| 6,953,461 B2 | 10/2005 | McClurken et al. |
| 6,981,628 B2 | 1/2006 | Wales |
| 7,008,421 B2 | 3/2006 | Daniel |
| 7,033,356 B2 | 4/2006 | Latterell |
| 7,063,699 B2 | 6/2006 | Hess et al. |
| 7,090,637 B2 | 8/2006 | Danitz et al. |
| 7,090,673 B2 | 8/2006 | Dycus et al. |
| 7,090,685 B2 | 8/2006 | Kortenbach et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,118,587 B2 | 10/2006 | Dycus et al. |
| 7,125,409 B2 | 10/2006 | Truckai et al. |
| 7,137,980 B2 | 11/2006 | Buysse et al. |
| 7,159,750 B2 | 1/2007 | Racenet et al. |
| 7,166,102 B2 | 1/2007 | Fleenor et al. |
| 7,169,146 B2 | 1/2007 | Truckai et al. |
| 7,179,254 B2 | 2/2007 | Pendekanti et al. |
| 7,195,627 B2 | 3/2007 | Amoah et al. |
| 7,220,260 B2 | 5/2007 | Fleming et al. |
| 7,238,195 B2 | 7/2007 | Viola |
| 7,250,048 B2 | 7/2007 | Francischelli et al. |
| 7,255,697 B2 | 8/2007 | Dycus et al. |
| 7,267,677 B2 | 9/2007 | Johnson et al. |
| 7,270,664 B2 | 9/2007 | Johnson et al. |
| 7,276,068 B2 | 10/2007 | Johnson et al. |
| 7,278,991 B2 | 10/2007 | Morris et al. |
| 7,291,143 B2 | 11/2007 | Swanson |
| 7,303,557 B2 | 12/2007 | Wham |
| 7,329,256 B2 | 2/2008 | Johnson et al. |
| 7,364,577 B2 | 4/2008 | Wham et al. |
| 7,367,972 B2 | 5/2008 | Francischelli et al. |
| 7,410,483 B2 | 8/2008 | Danitz et al. |
| 7,494,039 B2 | 2/2009 | Racenet et al. |
| 7,506,790 B2 | 3/2009 | Shelton, IV et al. |
| 7,513,898 B2 | 4/2009 | Johnson et al. |
| 7,540,872 B2 | 6/2009 | Schechter et al. |
| 7,549,564 B2 | 6/2009 | Boudreaux |
| 7,588,566 B2 | 9/2009 | Treat et al. |
| 7,624,902 B2 | 12/2009 | Marczyk et al. |
| 7,641,651 B2 | 1/2010 | Nezhat et al. |
| 7,651,492 B2 | 1/2010 | Wham |
| 7,703,653 B2 | 4/2010 | Shah et al. |
| 7,794,461 B2 | 9/2010 | Eder et al. |
| 7,803,156 B2 | 9/2010 | Eder et al. |
| 7,862,565 B2 | 1/2011 | Eder et al. |
| 8,147,485 B2 | 4/2012 | Wham |
| 2001/0029367 A1 | 10/2001 | Fleenor et al. |
| 2002/0062123 A1 | 5/2002 | McClurken et al. |
| 2002/0062136 A1 | 5/2002 | Hillstead et al. |
| 2002/0107514 A1 | 8/2002 | Hooven |
| 2002/0124853 A1 | 9/2002 | Burbank et al. |
| 2002/0128643 A1 | 9/2002 | Simpson et al. |
| 2002/0151882 A1 | 10/2002 | Marko et al. |
| 2002/0177848 A1 | 11/2002 | Truckai et al. |
| 2002/0183734 A1 | 12/2002 | Bommannan et al. |
| 2002/0183738 A1 | 12/2002 | Chee et al. |
| 2003/0004510 A1 | 1/2003 | Wham et al. |
| 2003/0015855 A1 | 1/2003 | McCoy |
| 2003/0018331 A1 | 1/2003 | Dycus et al. |
| 2003/0078577 A1 | 4/2003 | Truckai |
| 2003/0144652 A1 | 7/2003 | Baker et al. |
| 2003/0144653 A1 | 7/2003 | Francischelli et al. |
| 2003/0153908 A1 | 8/2003 | Goble |
| 2003/0158547 A1 | 8/2003 | Phan |
| 2003/0158551 A1 | 8/2003 | Paton et al. |
| 2003/0171745 A1 | 9/2003 | Francischelli et al. |
| 2003/0199863 A1* | 10/2003 | Swanson et al. ............... 606/40 |
| 2003/0199869 A1 | 10/2003 | Johnson et al. |
| 2003/0216726 A1 | 11/2003 | Eggers et al. |
| 2003/0229344 A1 | 12/2003 | Dycus et al. |
| 2003/0236549 A1 | 12/2003 | Bonadio et al. |
| 2004/0006339 A1 | 1/2004 | Underwood et al. |
| 2004/0010245 A1 | 1/2004 | Cerier et al. |
| 2004/0049185 A1 | 3/2004 | Latterell |
| 2004/0068274 A1 | 4/2004 | Hooven |
| 2004/0097919 A1 | 5/2004 | Wellman et al. |
| 2004/0106917 A1 | 6/2004 | Ormsby et al. |
| 2004/0122423 A1 | 6/2004 | Dycus et al. |
| 2004/0143263 A1 | 7/2004 | Schechter et al. |
| 2004/0167508 A1 | 8/2004 | Wham |
| 2004/0193148 A1 | 9/2004 | Wham et al. |
| 2004/0199226 A1 | 10/2004 | Shadduck |
| 2004/0236320 A1 | 11/2004 | Protsenko |
| 2004/0236326 A1 | 11/2004 | Schulze |
| 2005/0010212 A1 | 1/2005 | McClurken et al. |
| 2005/0015085 A1 | 1/2005 | McClurken et al. |
| 2005/0019654 A1 | 1/2005 | Kishida |
| 2005/0021024 A1 | 1/2005 | Hooven |
| 2005/0021026 A1 | 1/2005 | Baily |
| 2005/0021027 A1 | 1/2005 | Shields et al. |
| 2005/0033276 A1 | 2/2005 | Adachi |
| 2005/0033277 A1 | 2/2005 | Clague et al. |
| 2005/0033278 A1 | 2/2005 | McClurken et al. |
| 2005/0033282 A1 | 2/2005 | Hooven |
| 2005/0070895 A1 | 3/2005 | Ryan et al. |
| 2005/0070978 A1 | 3/2005 | Bek |
| 2005/0090819 A1 | 4/2005 | Goble |
| 2005/0096645 A1 | 5/2005 | Wellman et al. |
| 2005/0096694 A1 | 5/2005 | Lee |
| 2005/0101951 A1 | 5/2005 | Wham |
| 2005/0107781 A1 | 5/2005 | Ostrovsky et al. |
| 2005/0107784 A1 | 5/2005 | Moses et al. |
| 2005/0113817 A1 | 5/2005 | Isaacson et al. |
| 2005/0113820 A1 | 5/2005 | Goble et al. |
| 2005/0113826 A1 | 5/2005 | Johnson et al. |
| 2005/0119654 A1 | 6/2005 | Swanson et al. |
| 2005/0131390 A1 | 6/2005 | Heinrich et al. |
| 2005/0137591 A1 | 6/2005 | Barry et al. |
| 2005/0149073 A1 | 7/2005 | Arani et al. |
| 2005/0171530 A1 | 8/2005 | Hooven |
| 2005/0171533 A1 | 8/2005 | Latterell et al. |
| 2005/0187561 A1 | 8/2005 | Lee-Sepsick et al. |
| 2005/0192568 A1 | 9/2005 | Truckai et al. |
| 2005/0192633 A1 | 9/2005 | Montpetit |
| 2005/0196421 A1 | 9/2005 | Hunter et al. |
| 2005/0203500 A1 | 9/2005 | Saadat et al. |
| 2005/0203504 A1 | 9/2005 | Wham et al. |

(56) References Cited

U.S. PATENT DOCUMENTS

| | | |
|---|---|---|
| 2005/0209664 A1 | 9/2005 | Hunter et al. |
| 2005/0226682 A1 | 10/2005 | Chersky et al. |
| 2005/0256522 A1 | 11/2005 | Francischelli et al. |
| 2005/0256524 A1 | 11/2005 | Long et al. |
| 2005/0261676 A1 | 11/2005 | Hall et al. |
| 2006/0025765 A1 | 2/2006 | Landman et al. |
| 2006/0025812 A1 | 2/2006 | Shelton |
| 2006/0041254 A1 | 2/2006 | Francischelli et al. |
| 2006/0052778 A1 | 3/2006 | Chapman et al. |
| 2006/0052779 A1 | 3/2006 | Hammill |
| 2006/0064084 A1* | 3/2006 | Haemmerich et al. ......... 606/41 |
| 2006/0064085 A1 | 3/2006 | Schechter et al. |
| 2006/0064086 A1 | 3/2006 | Odom |
| 2006/0079872 A1 | 4/2006 | Eggleston |
| 2006/0142751 A1 | 6/2006 | Treat et al. |
| 2006/0167451 A1 | 7/2006 | Cropper |
| 2006/0189980 A1 | 8/2006 | Johnson et al. |
| 2006/0190029 A1 | 8/2006 | Wales |
| 2006/0199999 A1 | 9/2006 | Ikeda et al. |
| 2006/0217709 A1 | 9/2006 | Couture et al. |
| 2006/0226196 A1 | 10/2006 | Hueil et al. |
| 2006/0229665 A1 | 10/2006 | Wales et al. |
| 2006/0253117 A1 | 11/2006 | Hovda et al. |
| 2006/0258954 A1 | 11/2006 | Timberlake et al. |
| 2006/0259034 A1 | 11/2006 | Eder et al. |
| 2006/0259035 A1 | 11/2006 | Nezhat et al. |
| 2006/0271037 A1 | 11/2006 | Maroney et al. |
| 2006/0271038 A1 | 11/2006 | Johnson et al. |
| 2006/0271041 A1 | 11/2006 | Eder et al. |
| 2006/0271042 A1 | 11/2006 | Latterell et al. |
| 2006/0287674 A1 | 12/2006 | Ginn et al. |
| 2006/0289602 A1 | 12/2006 | Wales et al. |
| 2006/0293649 A1 | 12/2006 | Lorang |
| 2006/0293655 A1 | 12/2006 | Sartor |
| 2007/0005053 A1 | 1/2007 | Dando |
| 2007/0005061 A1 | 1/2007 | Eder et al. |
| 2007/0055231 A1 | 3/2007 | Dycus et al. |
| 2007/0062017 A1 | 3/2007 | Dycus et al. |
| 2007/0073340 A1 | 3/2007 | Shelton et al. |
| 2007/0128174 A1 | 6/2007 | Kleinsek et al. |
| 2007/0129726 A1 | 6/2007 | Eder et al. |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173811 A1 | 7/2007 | Couture et al. |
| 2007/0179497 A1 | 8/2007 | Eggers et al. |
| 2007/0185482 A1 | 8/2007 | Eder et al. |
| 2007/0208330 A1 | 9/2007 | Treat et al. |
| 2007/0244538 A1 | 10/2007 | Eder et al. |
| 2007/0250113 A1 | 10/2007 | Hegeman |
| 2007/0260242 A1 | 11/2007 | Dycus et al. |
| 2007/0265613 A1 | 11/2007 | Edelstein et al. |
| 2007/0282318 A1* | 12/2007 | Spooner et al. ................ 606/32 |
| 2007/0282320 A1 | 12/2007 | Buysse et al. |
| 2007/0299439 A1 | 12/2007 | Latterell et al. |
| 2008/0015562 A1 | 1/2008 | Hong |
| 2008/0039835 A1 | 2/2008 | Johnson et al. |
| 2008/0045947 A1 | 2/2008 | Johnson et al. |
| 2008/0114351 A1 | 5/2008 | Irisawa et al. |
| 2008/0114356 A1 | 5/2008 | Johnson et al. |
| 2008/0172052 A1 | 7/2008 | Eder et al. |
| 2008/0188844 A1 | 8/2008 | McGreevy et al. |
| 2008/0195093 A1 | 8/2008 | Couture et al. |
| 2008/0221565 A1 | 9/2008 | Eder |
| 2008/0228179 A1 | 9/2008 | Eder et al. |
| 2008/0275446 A1 | 11/2008 | Messerly |
| 2008/0308607 A1 | 12/2008 | Timm et al. |
| 2009/0018535 A1 | 1/2009 | Schechter et al. |
| 2009/0138006 A1 | 5/2009 | Bales et al. |
| 2009/0149853 A1 | 6/2009 | Shields et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171354 A1 | 7/2009 | Deville et al. |
| 2009/0182323 A1 | 7/2009 | Eder et al. |
| 2009/0198272 A1 | 8/2009 | Kerver et al. |
| 2009/0209953 A1 | 8/2009 | Schoenman |
| 2009/0234347 A1 | 9/2009 | Treat et al. |
| 2009/0240245 A1 | 9/2009 | Deville et al. |
| 2009/0299367 A1 | 12/2009 | Ginnebaugh et al. |
| 2010/0042093 A9 | 2/2010 | Wham et al. |
| 2010/0076427 A1 | 3/2010 | Heard |
| 2010/0094282 A1 | 4/2010 | Kabaya |
| 2010/0280508 A1 | 11/2010 | Eder |
| 2010/0298823 A1* | 11/2010 | Cao et al. ..................... 606/34 |
| 2011/0202058 A1 | 8/2011 | Eder |

FOREIGN PATENT DOCUMENTS

| | | |
|---|---|---|
| CN | 1882289 A | 12/2006 |
| EP | 487269 | 5/1991 |
| EP | 440385 | 7/1991 |
| EP | 502268 | 9/1992 |
| EP | 562195 | 9/1993 |
| EP | 658333 | 6/1995 |
| EP | 536998 | 4/1996 |
| EP | 518230 | 5/1996 |
| EP | 0737446 | 10/1996 |
| EP | 875209 | 4/1998 |
| EP | 878169 | 11/1998 |
| EP | 640315 | 12/1998 |
| EP | 923907 | 6/1999 |
| EP | 640317 | 9/1999 |
| EP | 771176 | 7/2000 |
| EP | 1050278 | 11/2000 |
| EP | 1064886 | 1/2001 |
| EP | 833593 | 2/2001 |
| EP | 1254637 | 11/2002 |
| EP | 0717960 B1 | 2/2003 |
| EP | 1293169 | 3/2003 |
| EP | 1293170 | 3/2003 |
| EP | 869742 | 5/2003 |
| EP | 1330989 | 7/2003 |
| EP | 1330991 | 7/2003 |
| EP | 1344498 | 9/2003 |
| EP | 873089 | 10/2003 |
| EP | 742696 | 11/2003 |
| EP | 1041933 B1 | 3/2004 |
| EP | 959784 | 4/2004 |
| EP | 0794735 | 7/2004 |
| EP | 1004277 | 7/2004 |
| EP | 959786 | 9/2004 |
| EP | 913126 | 10/2004 |
| EP | 956827 | 10/2004 |
| EP | 1472984 | 11/2004 |
| EP | 1025807 | 12/2004 |
| EP | 1486177 | 12/2004 |
| EP | 1518498 | 3/2005 |
| EP | 1518499 | 3/2005 |
| EP | 927543 | 4/2005 |
| EP | 1532933 | 5/2005 |
| EP | 1586281 | 10/2005 |
| EP | 1621146 | 2/2006 |
| EP | 1632192 | 3/2006 |
| EP | 1637086 | 3/2006 |
| EP | 1 645 234 A1 | 4/2006 |
| EP | 1645237 | 4/2006 |
| EP | 1747761 | 1/2007 |
| EP | 1767164 A1 | 3/2007 |
| EP | 1852081 | 11/2007 |
| EP | 1862138 | 12/2007 |
| EP | 1039862 B1 | 5/2008 |
| EP | 1707143 B1 | 6/2008 |
| EP | 1958583 | 8/2008 |
| EP | 2065006 | 6/2009 |
| EP | 2106764 | 10/2009 |
| EP | 2110093 | 10/2009 |
| JP | 09-501328 | 2/1997 |
| JP | A 11070123 | 3/1999 |
| JP | A 11070124 | 3/1999 |

(56) References Cited

FOREIGN PATENT DOCUMENTS

| | | |
|---|---|---|
| JP | 2001-518344 | 10/2001 |
| JP | A 2003/088534 | 3/2003 |
| JP | A 2004/049566 | 2/2004 |
| JP | A 2005/021703 | 1/2005 |
| JP | 2005-040616 A | 2/2005 |
| JP | 2005-512671 | 5/2005 |
| JP | 2005-517498 A | 6/2005 |
| JP | A 2005/144193 | 6/2005 |
| JP | 2007-195973 A | 8/2007 |
| JP | 2008-114042 A | 5/2008 |
| WO | WO 92/22257 | 12/1992 |
| WO | WO 93/08754 | 5/1993 |
| WO | WO 94/00060 | 1/1994 |
| WO | WO94/26179 A1 | 11/1994 |
| WO | WO 94/26228 | 11/1994 |
| WO | WO 95/02371 | 1/1995 |
| WO | 9509576 | 4/1995 |
| WO | WO 95/14436 | 6/1995 |
| WO | WO 95/25471 | 9/1995 |
| WO | WO 96/05776 | 2/1996 |
| WO | 9619152 | 6/1996 |
| WO | WO9616605 | 6/1996 |
| WO | WO 96/23449 | 8/1996 |
| WO | WO 97/24073 | 7/1997 |
| WO | WO 97/24074 | 7/1997 |
| WO | WO 97/24995 | 7/1997 |
| WO | WO 98/12999 | 4/1998 |
| WO | WO 98/43548 | 10/1998 |
| WO | WO 98/53750 | 12/1998 |
| WO | WO 99/17670 | 4/1999 |
| WO | WO 99/23933 | 5/1999 |
| WO | WO 99/51155 | 10/1999 |
| WO | WO 99/51158 | 10/1999 |
| WO | WO 99/52459 | 10/1999 |
| WO | WO 99/56646 | 11/1999 |
| WO | WO 00/13192 | 3/2000 |
| WO | WO 00/13193 | 3/2000 |
| WO | WO 00/47124 | 8/2000 |
| WO | 0051512 | 9/2000 |
| WO | WO0112090 | 2/2001 |
| WO | WO 01/35846 | 5/2001 |
| WO | WO 01/54602 | 8/2001 |
| WO | WO 01/58372 | 8/2001 |
| WO | WO01/58373 A1 | 8/2001 |
| WO | WO 01/82812 | 11/2001 |
| WO | WO 02/24092 | 3/2002 |
| WO | WO 02/36028 | 5/2002 |
| WO | WO 02/067798 | 7/2002 |
| WO | WO 02/058542 | 8/2002 |
| WO | WO 02/071926 | 9/2002 |
| WO | WO 03/024348 | 3/2003 |
| WO | WO 03/053266 A2 | 7/2003 |
| WO | WO03/088806 A2 | 10/2003 |
| WO | WO 03/096886 | 11/2003 |
| WO | WO 03/103522 | 12/2003 |
| WO | WO2004/032776 A1 | 4/2004 |
| WO | WO2004032596 | 4/2004 |
| WO | WO2004073490 | 9/2004 |
| WO | WO 2004/098383 | 11/2004 |
| WO | WO 2004/103156 | 12/2004 |
| WO | WO 2005/009213 | 2/2005 |
| WO | 2005030071 | 4/2005 |
| WO | WO 2005/034729 | 4/2005 |
| WO | WO 2005/079901 | 9/2005 |
| WO | WO 2005/115251 | 12/2005 |
| WO | WO2006/060431 A1 | 6/2006 |
| WO | WO 2006/124601 | 11/2006 |
| WO | WO2006124518 | 11/2006 |
| WO | WO2007/002227 A2 | 1/2007 |
| WO | WO2007/082061 A2 | 7/2007 |
| WO | WO2008/094554 A2 | 8/2008 |
| WO | WO2008094564 | 8/2008 |
| WO | WO2008/124112 A1 | 10/2008 |
| WO | WO2009070780 | 6/2009 |
| WO | WO2009154976 | 12/2009 |

OTHER PUBLICATIONS

Aoki, T. et al.; *Thoracoscopic Resection of the Lung With the Ultrasonic Sca lpel*; Apr. 1999 Ann Thorac Surg.; 67 (4): 1181-3; Department of Thoracic Surgery, Saiseikai Kanagawaken Hospital, Yokohama, Japan.

*Arthrocare Receives Clearance to Market Coblation-Based Devices for Gynecology and Laparoscopic Surgery; Clearance Includes Plasma Forceps and 21 Specific Indications*; Oct. 25, 2001; Business Wire, p. 0524.

Bergamaschi, R. et al.; *Laparoscopic Intracorporeal Bowel Resection With Ultrasound Versus Electrosurgical Dissection*; Jan.-Mar. 2001; JSLS. 5 (1): 17-20; National Center for Advanced Laparoscopic Surgery, Tondheim, Norway. r.bergamaschi@altavista.net.

Berguer, Ramon et al.; *SAGES 2001 Hands-On Course I—Taking It To The Next Level: Advanced Laparoscopic Techniques*; http://www.sages.org/01program/syllabi/ho1/ho1.html#schirme.

Briani, S. et al.; *Pseudo-Bipolar Electrocoagulation With a Branched Forceps*; 1967; Minerva Neurochir.; 11 (3): 306-11.

Cakan, A. et al.; *The Histological Effect of Harmonic Scalpel and Electrocautery in Lung Resections. An Experimental Study in a Rat Model*; Feb. 2004; J Cardiovasc Surg (Torino).; 45 (1): 63-5; Department of Thoracic Surgery, Ege University School of Medicine, Izmir, Turkey. alpcakan@gohip.com.

Ceviker, N. et al.; *A New Coated Bipolar Coagulator: Technical Note*; 1998; Acta Neurochir (Wien).; 140 (6): 619-20; Department of Neurosurgery, Faculty of Medicine, Gazi University, Ankara, Turkey.

Cherchi, PL, et al.; *Utility of Bipolar Electrocautery Scissors for Cervical Conization*; 2002; Eur J Gynaecol Oncol. 2002; 23 (2): 154-6; Department of Pharmacology, Gynecology and Obstetrics, University of Sassari, Italy.

*Circon Corporation—Company Report*; Investext, p. 1-13; Jan. 3, 1995.

Colvin, D.P. et al.; *Development of an Endoscopic RF Hyperthermia System for Deep Tumor Therapy*; 1987; American Society of Mechanical Engineers, Heat Transfer Division, (Publication) HTD v. 95. Publ by ASME (BED-v 7), New York, NY, USA p. 25-30.

Corson, S.L.; *Two New Laparoscopic Instruments: Bipolar Sterilizing Forceps and Uterine Manipulator*; Jan.-Feb. 1977; Medical Instrumentation vol. 11, No. 1 p. 7-8;; USA.

*Curon Medical Announces Presentation of Positive Clinical Study Results of Stretta(R) Procedure for Gastroesophageal Reflux Disease (GERD)*; Mar. 20, 2002; PR Newswire, pNYW07920032002.

*Curon Announces The Publication of Data Supporting Durability and Effectiveness of Stretta (R) System;—Positive One Year Follow-Up Data of U.S. Clinical Trial Published in Gastrointestinal Endoscopy*; Feb. 7, 2002; PR Newswire, pNYTH10307022002.

Daniel, P. et al.; *Ultrasonic Sealing of the Lung Parenchyma After Atypical Resection; Z Exp Chir Transplant Kunstliche Organe*. 1987; 20 (2): 117-21.

DiGeronimo, EM et al.; *Cut-Blot-Coagulate: A New Time Saving Device*; Nov. 1982 Plast Reconstr Surg.; 70 (5): 639-40.

Dubuc-Lissoir, J.; *Use of a New Energy-Based Vessel Ligation Device During Laparoscopic Gynecologic Oncologic Surgery*; Mar. 2003 Surg Endosc.; 17 (3): 466-8. Epub Oct. 31, 2002; Department of Obstetrics and Gynecology, CHUM—Notre-Dame Hospital, Pavillon Charles-Simard, 2065 Alexandre-de-Seve, 4th Floor, Montreal, Quebec, Canada, H2L 2W5. josee.dubuc-lissoir.chum@ssss.gouv.gc.ca.

Eichfeld U., et al.; *Evaluation of Ultracision in Lung Metastatic Surgery*; Oct. 2000 Ann Thorac Surg.; 70 (4): 1181-4; Department of Surgery I, General Surgery, Surgical Oncology and Thoracic Surgery, and Institute of Pathology, University of Leipzig, Germany. eichu@medizin.uni-leipzig.de.

*Enable Medical Introduces Second Generation Bipolar Scissors*; Dec. 1998; Health Inudstry Today, pNA.

Ercoli, A. et al.; *Radiofrequency Bipolar Coagulation for Radical Hysterectomy: Technique, Feasibility and Complications*; Mar.-Apr. 2003 Int J Gynecol Cancer.; 13 (2): 187-91;Department of Obstetrics and Gynecology, Catholic University, Rome, Italy 187-91.

(56) References Cited

OTHER PUBLICATIONS

*Everst Medical Announces Introductio of 3mm Bipolar Forceps*; Oct. 2, 1006; PR Newswire, p1002MNW021.
*Everest Medical Discusses Patent Status; Forecasts $1 Million Revenue First Quarter; Introduces Next Generation Bipolar Scissors*; Mar. 31, 1994; PR Newswire, pN/A.
*Everest Medical Introduces New Quadripolar (TM) Cutting Forceps at The Global Congress of Gynecologic Endoscopy Meeting*; Nov. 8, 1999; PR Newswire p. 8927.
*Everest Medical Releases Bicoag (TM) for Use in Treating Bleeding Ulcers*; May 9, 1990; News Release, p. 1.
*Everest Medical Reports Record First Quarter Results; Introduces Next Generation Bipolar Scissors*; Apr. 19, 1994; PR newswire, pN/A.
Forestier D. et al.; *Do Bipolar Scissors Increase Postoperative Adhesions? An Experimental Double-Blind Randomized Trial*; Nov. 2002 Ann Chir.; 127 (9): 680-4; Service de chirurgie generale et digestive, Hotel-Dieu, boulevard Leon-Malfreyt, 63058 Clermont-Ferrand, France.
Gerasin VA et al.; *Endoscopic Electrosurgery of the Trachea and Bronchi*; Sep.-Oct. 1988 Grudn Khir.; (5): 50-3.
Gyr, T. et al.; *Minimal Invasive Laparoscopic Hysterectomy With Ultrasonic Scalpel*; Jun. 2001 Am J Surg.; 181 (6): 516-9; Department of Obstetrics and Gynecology, Regional Hospital, Lugano, Switzerland.
Gyrus Medical: *Cutting Forceps*; http://www.gyrusgroup.com/medical/products_item.asp?id=7.
Gyrus Medical: *Lyons TM Dissecting Forceps*; http://www.gyrusgroup.com/medical/products_item.asp?id=8.
*Gyrus Medical: LP Scissors*; http://www.gyrusgroup.com/medical/products_item.asp?id=11.
Gyrus Medical: *Micro/Macro-Jaw Forceps*; http://www.gyrusgroup.com/medical/products_item.asp?id=13.
Gyrus Medical: *Seal TM Open Forceps*; http://www.gyrusgroup.com/medical/products_item.asp?id=15.
Harrell, AG et al.; *Energy Sources in Laparoscopy*; Sep. 2004 Semin Laparosc Surg.; 11 (3): 201-9; Carolinas Laparoscopic and Advanced Surgery Program, Carolinas Medical Center, Charlotte, NC 28203, USA.
Hayashi A. et al.; *Experimental and Clinical Evaluation of the Harmonic Scalpel in Thoracic Surgery*; 1999; Kurume Med J.; 46 (1): 25-9; Department of Surgery, Kurume University School of Medicine, Japan.
Hefni, MA et al.; *Safety and Efficacy of Using the Ligasure Vessel Sealing System for Securing the Pedicles in Vaginal Hysterectomy: Randomised Controlled Trial*; Bjog. Mar. 2005; 112 (3): 329-33; Department of Gynecology, Benenden Hospital, Kent TN17 7AX, UK.
Heniford BT et al.; *Initial Results With an Electrothermal Bipolar Vessel Sealer*; Aug. 2001 Surg Endosc.; 15 (8): 799-801. Epub May 14, 2001; Carolinas Laparoscopic and Advanced Surgery Program, Department of General Surgery, Caro;inas Medical Center, 1000 Blythe Boulevard, MEB # 601, Charlotte, NC, USA.
Kamat, AA et al.; *Superiority of Electrocautery Over the Suture Method for Achieving Cervical Cone. Bed Hemostasis*; Oct. 2003 Obstet Gynecol.; 102 (4): 726-30; Department of Obstetrics and Gynecology, Baylor College of Medicine, Houston, Texas 77030, USA. akamat@bcm.tmc.edu.
Kato, K. et al.; *A Computer Based, Temperature Controlled Bipolar Electrocoaqulation System*; Sep. 1996 Eur J Obstet Gynecol Reprod Biol.; 68 (1-2): 119-22; Department of Obstetrics and Gynecology, University of Essen, Germany.
Kennedy, JS et al.; *High-Burst-Strength, Feedback-Controlled Bipolar Vessel Sealing*; Jun. 1998 Surg Endosc.; 12 (6): 876-8; Valleylab, Inc., 5920 Longbow Drive, Boulder, CO 80301, USA.
Kim, Byungkyu et al.; *Design and Fabrication of a Locomotive Mechanism for Capsule-Type Endoscopes Using Shape Memory Alloys (Smas)*; Feb. 2005. IEEE/ASME Transactions on Mechatronics, vol. 10, No. 1, p. 77-86; USA.

Koch, C. et al.; *Determination of Temperature Elevation in Tissue During the Application of the Harmonic Scalpel*; Feb. 2003 Ultrasound Med Biol.; 29 (2): 301-9; Ultrasonics Section, Physikalisch-Technische Bundesanstalt Braunschweig, B raunschweig, Germany. christian.koch@ptb.de.
Kohler C. et al.; *Laparoscopic Coagulation of the Uterine Blood Supply in Laparoscopic-Assisted Vaginal Hysterectomy Is Associated With Less Blood Loss*; 2004 Eur J Gynaecol Oncol.; 25 (4): 453-6; Department of Gynecology, Friedrich Schiller University, Jena, Germany.
Kung, RC et al; *A New Bipolar System for Performing Operative Hysetroscopy in Normal Saline*; Aug. 1999; 6 (3): 331-6J Am Assoc Gynecol Laparosc. http://www.ncbi.nlm.nih.gov/entrez/guery.fcgi?cmd=Retrieve&db=pubmed&dopt=Abstract&list_uids=10459037&query_h1=1.
Kwok, A. et al.; *Comparison of Tissue Injury Between Laparosonic Coagulating Shears and Electrosurgical Scissors in the Sheep Model*; Aug. 2001 J Am Assoc Gynecol Laparosc.; 8 (3): 378-84; Department of Endosurgery, Women's Institute, University of Sydney, Australia.
Landman J. et al.; *Evaluation of a Vessel Sealing System, Bipolar Electrosurgery, Harmonic Scalpel, Titanium Clips, Endoscopic Gastrointestinal Anastomosis Vascular Staples and Sutures for Arterlal and Venous Ligation in a Porcine Model*; Feb. 2003 J Urol.; 169 (2): 697-700; Department of Surgery (Division of Urology), Washington University School of Medicine, St. Louis, Missouri, USA.
Lantis, JC II et al.; *Comparison of Coagulation Modalities in Surgery*; Dec. 1998 J Laparoendosc Adv Surg Tech A.; 8 (6): 381-94; Surgical Research Laboratory, New England Medical Center, Boston, Massachusetts, USA.
*Laparoscopic Lasers Vs. Electrosurgery: Debated Technology Choices*; Jun. 6, 1991; The BBI Newsletter, v.14, n. 6, pN/A.
Levy, Barbara et al.; *Update on Hysterectomy: New Technologies andTechniques*; Feb. 2003; http://www.obgmanagement.com/supplements/pdf/hysterectomy.pdf; A supplement to OBGg Management.
Levy, Barbara; *Use of a New Vessel Ligation Device During Vaginal Hysterectomy*; As presented at FIGO 2000, Washington, D.C.; University of Washington School of Medicine; Federal Way, Washington, USA; © 2000 Valleylab.
Lin, J. et al.; *Application of Ultrasonic Scalpel in Gynecologic Operative Laparoscopy*; Dec. 2001 Chin Med J (Engl.); 114 (12): 1283-5; Department of Gynecology, Women's Hospital, Medical School of Zhejiang University, Hangzhou 310006, China. Zuying@mail.hz.zj.cn.
Lyons, TL et al.; *An Innovative Bipolar Instrument for Laparoscopic Surgery*; JSLS. Jan.-Mar. 2005; 9 (1): 39-41; Center for Women's Care & Reproductive Surgery, Atlanta, Georgia, USA cwcrs@mindspring.com.
*Market and Technology Updates: Bipolar Endoscopic Device*; Jan. 24, 1990; The BBI Newsletter, v.13, n. 1, pN/A.
Matsumura Y. et al.; *New Surgical Technique of Pulmonary Segmentectomy by Ultrasonic Scalpel and Absorbable Sealing Materials*; Jan. 2004 Kyobu Geka.; 57 (1): 31-7; Department of Thoracic Surgery, Institute of Development, Aging and Cancer, Tohoku University, Sendai, Japan.
Mundt, C. et al.; *Advanced Sensor Systems for Improved Labor and Fetal Monitoring*; 1998; ISA TECH/EXPO Technology Update Conference Proceedings v. 2 n. 2, p. 79-89; 1998.
Nikolov, N. et al.; *Remote Controllable Vessel Occlusion Device*; Jan. 1978 Med Biol Eng Comput.; 16 (1): 116-7.
*U.S. Patent Issued for Novare Surgical Systems Cygnet (R) Surgical Clamp; Novare Signs Multi-Year Supply Agreement With Boston Scientific*, PR Newsire, pNA; Sep. 2, 2003.
Ou, CS et al.; *Total Laparoscopic Hysterectomy Using Multifunction Grasping, Coagulating, and Cutting Forceps*; Apr. 2004 J Laparoendosc Adv Surg Tech A.; 14 (2): 67-71; Department of Research and Development, Northwest Hospital and University of Washington School of Medicine, Seattle, Washington 98155, USA. cou@nwhsea.org.
Pavlov, Iuv et al.; *Ultrasonic Technologies in Diagnosis and Treatment of Patients With Surgical Diseases of Lungs and Pleura*; 2003 Khirurgiia (Mosk).; (8): 30-4.

(56) References Cited

OTHER PUBLICATIONS

Petrakis, IE et al.; *Use of the Ligasure Vessel Sealer in Total Abdominal Hysterectomy*; Jun. 2005 Int J Gynaecol Obstet.; 89 (3): 303-4. Epub Mar. 2, 2005; Department of General Surgery, University General Hospital of Heraklion, University of Crete, Heraklion, Crete, Greece. petrakis@post.com.
*Quadripolar Cutting Forceps Introduced by Everest Medical*; Jan. 2000; Health Industry Today, v. 63, n. 1, pNA.
*Radiofrequency Energy Proven Effective Against Leading Cause of Obstructive Sleep Apnea*; Sep. 14, 1998; Business Wire, p. 09140175.
Raestrup, H. et al.; *Dissection Technique—Is Ultrasound the Best Method?*; 2001 Kongressbd Dtsch Ges Chir Kongr.; 118: 69-70; Universitatsklinik Fur Allgemeine Chirurgie, Hoppe-Seyler-Strasse 3, 72076 Tubingen.
Robinson JL et al.; *Bipolar Diathermy*; Sep. 1974 Can J Surg.; 17 (5): 287-91.
Srisombut, C. et al.; *Laparoscopic Hysterectomy Using Laparosonic Coagulating Shears: Experience of 15 Cases*; Aug. 2000 J Med Assoc Thai.; 83 (8): 915-20; Department of Obstetrics and Gynecology, Faculty of Medicine, Ramathibodi Hospital, Mahidol University, Bangkok, Thailand.
Stanojevic, D. et al.; *An Ultrasonic Scalpel for Laparoscopic Gynecologic Surgery*; May-Jun. 1998 Srp Arh Celok Lek.; 126 (5-6): 214-6; Narodni Front Department of Gynecology and Obstetrics, Dr. Dragisha Mishovitsh Medical Centre, Belgrade.
Sugi, K. et al.; *Use of the Bipolar Vessel Sealing System in Lung Resection*; Jul. 2003 Kyobu Geka.; 56 (7): 551-4; Department of Clinical Research, National Sanyo Hospital, Ube, Japan.
Tajiri M. et al.; *Evaluation of an Ultrasonic Cutting and Coagulating System (Harmonic Scalpel) for Performing a Segmental and Wedge Resection of the Lung*; Dec. 1998 Kyobu Geka.; 51 (13): 1116-9; Department of Surgery, Kan to Rosai Hospital, Kawasaki, Japan.
Tamussino, K. et al.; *Electrosurgical Bipolar Vessel Sealing for Radical Abdominal Hysterectomy*; Feb. 2005 Gynecol Oncol.; 96 (2): 320-2;Department of Obstetrics and Gynecology, Medical University of Graz, Auenbruggerplatz 14, A-8036 Graz, Austria. Karl. tamussino@meduni-graz.at.
The Gynecare Versapoint; http://www.jnjgateway.com/home. jhtml?loc=USENG&page=viewContent&contentId=edea000100001747&parentID=fc0de00100000334; All contents copyright © Johnson & Johnson Gateway, LLC 2000-2005.
Timor-Tritsch Ie et al.; *Transvaginal Ultrasound-Assisted Gynecologic Surgery: Evaluation of a New Device to Improve Safety of Intrauterine Surgery*; Oct. 2003 Am J Obstet Gynecol.; 189 (4): 1074-9; Department of Obstetrics and Gynecology, New York University School of Medicine, NY 10016, USA. ilan.timor@med.nyu.edu.
Tucker, RD et al.; *Bipolar Electrosurgical Sphincterotomy*; Gastrointest Endosc. Mar.-Apr. 1992; 38 (2): 113-7; Department of Pathology, University of Iowa Hospitals Clinics, Iowa City 52242.
Tucker, R.D. et al.; *Capacitive Coupled Stray Currents During Laparoscopic and Endoscopic Electrosurgical Procedures*; Jul.-Aug. 1992; Biomedical Instrumentation & Technology vol. 26, No. 4, p. 303-311;; USA.
*Valley Forge Scientific Corp.—Company Report*; Jan. 27, 1993; Investext, p. 1-1.
Valleylab Products—*Electrosurgical Forceps: The Surgeon's Choice for Quality and Precision*; http://www.valleylab.com/product/es/accessories/forceps_over.html; © 2005 valleylab.
Valleylab Products—Ligasure TM Vessel Sealing System; http://www.valleylab.com/product/vessel_seal/index.html.
Weyl, BP; *How to Increase the Proportion of Vaginal Hysterectomies-Bipolar Coagulation*; Sep. 1999 Am J Obstet Gynecol.; 181 (3): 768.
Wilson, Fred; *Cool Tool, Hot New Application: Radiofrequency Energy Removes Head, Neck Tumors.* (*Dermatologic Surgery*); Aug. 2003; Dermatology Times, v. 24, n. 8, p. 54.

Zhi, Xu-Ting et al.; *Management of Gastroesophageal Reflux Disease: Medications, Surgery, or Endoscopic Therapy?* (*Current Status and Trends*); 2005; Journal of Long-Term Effects of Medical Implants v. 15 n. 4 2005. p. 375-388.
Nezhat et al.; U.S. Appl. No. 08/948,282 entitled "Method and systems for organ resection," filed Oct. 9, 1997.
Eder, Joseph C.; U.S. Appl. No. 12/200,798 entitled "Assisted systems and methods for performing transvaginal hysterectomies," filed Aug. 28, 2008.
Koss et al.; U.S. Appl. No. 12/748,229 entitled "Impedance mediated power delivery for electrosurgery," filed Mar. 26, 2010.
Koss et al.; U.S. Appl. No. 12/907,646 entitled "Impedance mediated control of power delivery for electrosurgery," filed Oct. 19, 2010.
Walberg, Erik; U.S. Appl. No. 13/021,633 entitled "Laparoscopic radiofrequency surgical device," filed Feb. 4, 2011.
Erbe Elektromedizin GmbH; ERBE BiClamp Brochure; http://www.erbe-med.com/erbe/media/Marketingmaterialien/85100-139_ERBE_EN_BiClamp_D024676.pdf; downloaded Jan. 24, 2011; 6 pgs.
Gyrus ACMI (an Olympus Company); PKS Seal (product page); http://www.gyrusacmi.com/user/display.cfm?display=product&pid=9024; downloaded Jan. 24, 2011; 1 page.
Kovac; Transvaginal hysterectomy: rationale and surgical approach; Obstet. Gynecol.; vol. 103; pp. 1321-1325; 2004.
Live Tissue Connect Technologies; company profile; (http://www.onemedplace.com/database/compdisplay_print.php?CompanyID=11508); 1 pg.; Oct. 19, 2010 (downloaded Feb. 7, 2011).
McClurken et al.; Collagen shrinkage and vessel sealing; Technical brief #300. Dover, NH: Tissue Link Medical; 2001.
Nojarov et al.; High-energy scissors mode; Phys Rev C Nucl Phys; vol. 51; No. 5; pp. 2449-2456; 1995 (http://arxiv.org/abs/nucl-th/9502001v1).
Parikh et al.; Three dimensional virtual reality model of the normal female pelvic floor; Annals of Bimedical Engineering; vol. 32; pp. 292-296; Feb. 2004.
Sages 2001 Nurses Program, Session 1; http://sages.org/01program/syllabi/nurse/nurse.html; downloaded Jan. 24, 2011; 5 pgs.
Surgrx 510(K) Summary (# K031133); Palo Alto, CA; 5 pgs.; Jul. 3, 2003.
Treat; A new thermal device for sealing and dividing blood vessels; http://www.starioninstruments.com/PDFs/Treat.pdf; downloaded Jun. 29, 2005; 2 pgs.
Tyco Healthcare; The LigaSure Vessel Sealing System (Brochure); Apr. 2002; 8 pgs.
Kerver et al.; U.S. Appl. No. 13/070,391 entitled "Articulable electrosurgical instrument with a stabilizable articulation actuator," filed Mar. 23, 2011.
Van Lue et al.; U.S. Appl. No. 13/110,848 entitled "Electrosurgical tissue sealing augmented with a seal-enhancing composition," filed May 18, 2011.
Chinese Application Serial No. 200880005613.7, Third Office Action mailed Aug. 30, 2013.
Canadian Application No. 2,677,300, Examination Report mailed Apr. 18, 2013.
Canadian Application No. 2,723,016, Office Action mailed Nov. 12, 2013.
Examination Report issued in Japanese Patent Application No. 2012 173318, dispatched on Aug. 26, 2013.
Chinese Application No. 200880005429.2, Second Office Action mailed Mar. 6, 2013 with English translation.
Examination Report issued in corresponding Japanese Patent Application No. 2011-509759, dispatched on Aug. 6, 2013.
Japanese Examination Report with English Translation issued in related Japanese Application No. 2011-205759, dated Feb. 28, 2014.
Indian Examination Report issued in related Indian Application No. 4341/KOLNP/2007, dated Feb. 27, 2014.
Korean Examination Report issued in related Korean Application No. 10-2009-7018104, dated Feb. 20, 2014.
Office Action mailed Jun. 8, 2015 for U.S. Appl. No. 12/410,322.
Refractec, Inc.; Medical Use of Radiofrequency (RF) Energy; (http://www.locateadoc.com/Site_Tools/Print.cfm); 2 pgs; Aug. 23, 2008.
Office Action mailed Jul. 30, 2015 in U.S. Appl. No. 13/637,533.

(56) References Cited

OTHER PUBLICATIONS

Indian First Examination Report issued in related Indian Appln. No. 2843/KOLNP/2009 dated Jul. 31, 2014.
U.S. Appl. No. 12/410,322, Non-Final Office Action mailed Oct. 17, 2012.
Australian Examination Report for Application No. 2008214068, dated Jan. 28, 2011.
Australian Examination Report for Application No. 2008275543, dated Nov. 9, 2010.
Canadian Examination Report for Application No. 2,677,300, dated Aug. 25, 2011.
Canadian Examination Report for Application No. 2,677,444, dated Aug. 18, 2011.
Chinese Application Serial No. 200880005429.2, First Office Action mailed Aug. 20, 2012.
Chinese Application Serial No. 200880005613.7, Second Office Action mailed Jan. 31, 2013, 11 pgs. (English Translation).
Chinese Notice of First Office Action with Text of Office Action issued in related Chinese Application No. 201180009484.0, dated Sep. 29, 2014.
Entire patent prosecution history of U.S. Appl. No. 11/382,635 filed, May 10, 2006, entitled, "Method for Tissue Cauterization," now U.S. Pat. No. 7,862,565, issued Jan. 4, 2011.
Entire patent prosecution history of U.S. Appl. No. 11/671,891, filed Feb. 6, 2007, entitled, "Electrocautery Method and Apparatus," now U.S. Pat. No. 8,696,662, issued Apr. 15, 2014.
Entire patent prosecution history of U.S. Appl. No. 11/671,911, filed Feb. 6, 2007, entitled, "Electrocautery Method and Apparatus," now U.S. Pat. No. 8,728,072, issued May 20, 2014.
Entire patent prosecution history of U.S. Appl. No. 12/062,516, filed Apr. 4, 2008, entitled, "Electrocautery Method and Apparatus."
Entire patent prosecution history of U.S. Appl. No. 12/410,322, filed Mar. 24, 2009, entitled, "Electrocautery Method and Apparatus."
Entire patent prosecution history of U.S. Appl. No. 13/096,912, filed Apr. 28, 2011, entitled, "Apparatus for Tissue Cauterization," now U.S. Pat. No. 8,888,770, issued Nov. 18, 2014.
Entire patent prosecution history of U.S. Appl. No. 13/637,533, filed Jan. 23, 2013, entitled, "Impedance Mediated Control of Power Delivery for Electrosurgery."
European Application Serial No. 08728715.7, European Examination Report dated Dec. 20, 2012.
European Patent Office Examination Report for Application No. EP 07 758 098.3 Dated Feb. 8, 2012.
European Search Report for Application No. PCT/US2008/052656 dated Mar. 30, 2012.
European Search Report issued in Application No. 11760294.6, dated Oct. 28, 2013.
Examination Report for Canadian Application No. 2,677,300 dated Mar. 28, 2012.
Examination Report for Canadian Application No. 2,677,444 dated Jul. 3, 2012.
Final Office Action for U.S. Appl. No. 12/062,516 dated Jul. 27, 2012.
International Application Serial No. PCT/US2011/029958, International Search Report dated Dec. 22, 2011.
Japanese Examination Report for Application No. 2009-549182, dated Oct. 27, 2011 with English translation.
Japanese Examination Report for Application No. 2009-549183, dated Oct. 27, 2011 with English translation.
Office Action for U.S. Appl. No. 12/062,516 mailed Mar. 16, 2015.
Office Action for U.S. Appl. No. 13/637,533 mailed Mar. 12, 2015.
Japanese Examination Report with English Translation issued in related Japanese Application No. 2013-501509, dated Nov. 7, 2014.
Notice of Allowance corresponding to U.S. Appl. No. 13/096,912, dated Jul. 25, 2014.
Final Office Action dated Dec. 30, 2015 for U.S. Appl. No. 12/062,516.
Notice of Allowance mailed Oct. 26, 2015 for U.S. Appl. No. 13/637,533.
Final Office Action mailed Apr. 6, 2016 for U.S. Appl. No. 12/410,322.

\* cited by examiner

ELECTROCAUTERY METHOD AND APPARATUS

CROSS-REFERENCE TO RELATED APPLICATIONS

This application is a continuation-in-part of U.S. patent application Ser. No. 11/671,891, filed Feb. 6, 2007, issued as U.S. Pat. No. 8,696,662, which, in turn, is a continuation-in-part of U.S. patent application Ser. No. 11/382,635 filed May 10, 2006, issued as U.S. Pat. No. 7,862,565, and Ser. No. 11/371,988 filed Mar. 8, 2006, issued as U.S. Pat. No. 7,803,156, and which claims the benefit thereof in accordance with 35 USC 120. U.S. application Ser. No. 11/382,635 filed May 10, 2006, issued as U.S. Pat. No. 7,862,565, in turn, claims the benefit of provisional applications 60/725,720 filed on Oct. 11, 2005 and 60/680,937 filed on May 12, 2005. The entireties of the foregoing applications are incorporated herein by this reference thereto.

BACKGROUND OF THE INVENTION

1. Field of the Invention

The invention relates to tissue cauterization. More particularly, the invention concerns an electrocautery system with various electrodes and a mechanism for automated or user-selected operation or compensation of the electrodes.

2. Description of the Related Art

Various physiological conditions call for tissue and organ removal. A major concern in all tissue removal procedures is hemostasis, that is, cessation of bleeding. All blood vessels supplying an organ or a tissue segment to be removed have to be sealed, either by suturing or cauterization, to inhibit bleeding when the tissue is removed. For example, when the uterus is removed in a hysterectomy, bleeding must be inhibited in the cervical neck, which must be resected along the certain vessels that supply blood to the uterus. Similarly, blood vessels within the liver must be individually sealed when a portion of the liver is resected in connection with removal of a tumor or for other purposes. Achieving hemostasis is necessary in open surgical procedures as well as minimally invasive surgical procedures. In minimally invasive surgical procedures, sealing of blood vessels can be especially time consuming and problematic because there is limited access via a cannula and other small passages.

Achieving hemostasis is particularly important in limited access procedures, where the organ or other tissue must be morcellated prior to removal. Most organs are too large to be removed intact through a cannula or other limited access passage, thus requiring that the tissue be morcellated, e.g. cut, ground, or otherwise broken into smaller pieces, prior to removal.

In addition to the foregoing examples, there exists a variety of other electrosurgical instruments to seal and divide living tissue sheets, such as arteries, veins, lymphatics, nerves, adipose, ligaments, and other soft tissue structures. A number of known systems apply radio frequency (RF) energy to necrose bodily tissue. Indeed, some of these provide significant advances and enjoy widespread use today. Nevertheless, the inventors have sought to identify and correct shortcomings of previous approaches, and to research possible improvements, even when the known approaches are adequate.

In this respect, one problem recognized by the inventors concerns the small size of today's electrode structures. In particular, many electrosurgical instrument manufacturers limit the total length and surface area of electrodes to improve the likelihood of completely covering the electrodes with tissue. This small electrodes strategy results in the surgeon having to seal and divide multiple times to seal and divide long tissue sheets adequately. Such time consuming processes are also detrimental to patients, increasing anesthetic time and potentially increasing the risk of injury to surrounding structures, as the delivery of energy and division of tissue is repeated again and again.

The consequences of partial electrode coverage can be significant. This condition can cause electrical arcing, tissue charring, and inadequate tissue sealing. Mechanical, e.g. blade, or electrosurgical division of tissue is performed immediately following tissue sealing, and the division of inadequately sealed tissue can pose a risk to the patient because unsealed vessels may hemorrhage. Arcing presents its own set of problems. If electrocautery electrodes generate an arc between them, instead of passing RF energy through targeted tissue, the tissue fails to undergo the intended electrocautery. Furthermore, depending upon the path of the arc, this might damage non-targeted tissue. Another problem is that adjacent electrodes in a multiple electrode system may generate electrical cross-talk or generate excessive thermal effect in the transition zone between two adjacent electrodes that fire sequentially. Previous designs prevented this by imposing a mechanical standoff for the jaws that the electrodes were fastened onto. However, this standoff prevented very thin tissue from making contact with the opposing electrodes, preventing an optimal electrical seal in these regions. These standoffs, if too shallow, can also result in arcing between electrodes.

At typical radiofrequency energy (RF) frequencies in the 300 kHz to 10 MHz range, tissue impedance is largely resistive. Prior to tissue desiccation, initial impedances can vary greatly depending on the tissue type and location, vascularity, etc. Thus, to ascertain the adequacy of tissue electrode coverage based solely on local impedance is imprecise and impractical. A feasible and dependable methodology for determining electrode coverage by tissue would allow for the development of electrodes of greater length and surface area for use in the safe and rapid sealing and division of tissue sheets during surgical procedures. It would therefore be advantageous to provide a methodology for determining the area of tissue coverage of one or more electrodes.

SUMMARY

An electrode structure and a mechanism for automated or user-selected operation or compensation of the electrodes, for example to determine tissue coverage and/or prevent arcing between bottom electrodes during electrocautery is disclosed.

DETAILED DESCRIPTION

In view of the problems of conventional technology that the inventors have recognized (as discussed above), the inventors have sought to improve the ability of a user to control electrocautery electrodes after said electrode have been inserted into the body. Further areas of their focus include improving the efficiency of transferring power to electrode structures, and improving the accuracy of measurements taken from the electrode structure in situ. One benefit of implementing these improvements is the ability to use larger electrode surfaces, with the advantageous consequences discussed above.

Figure 1:
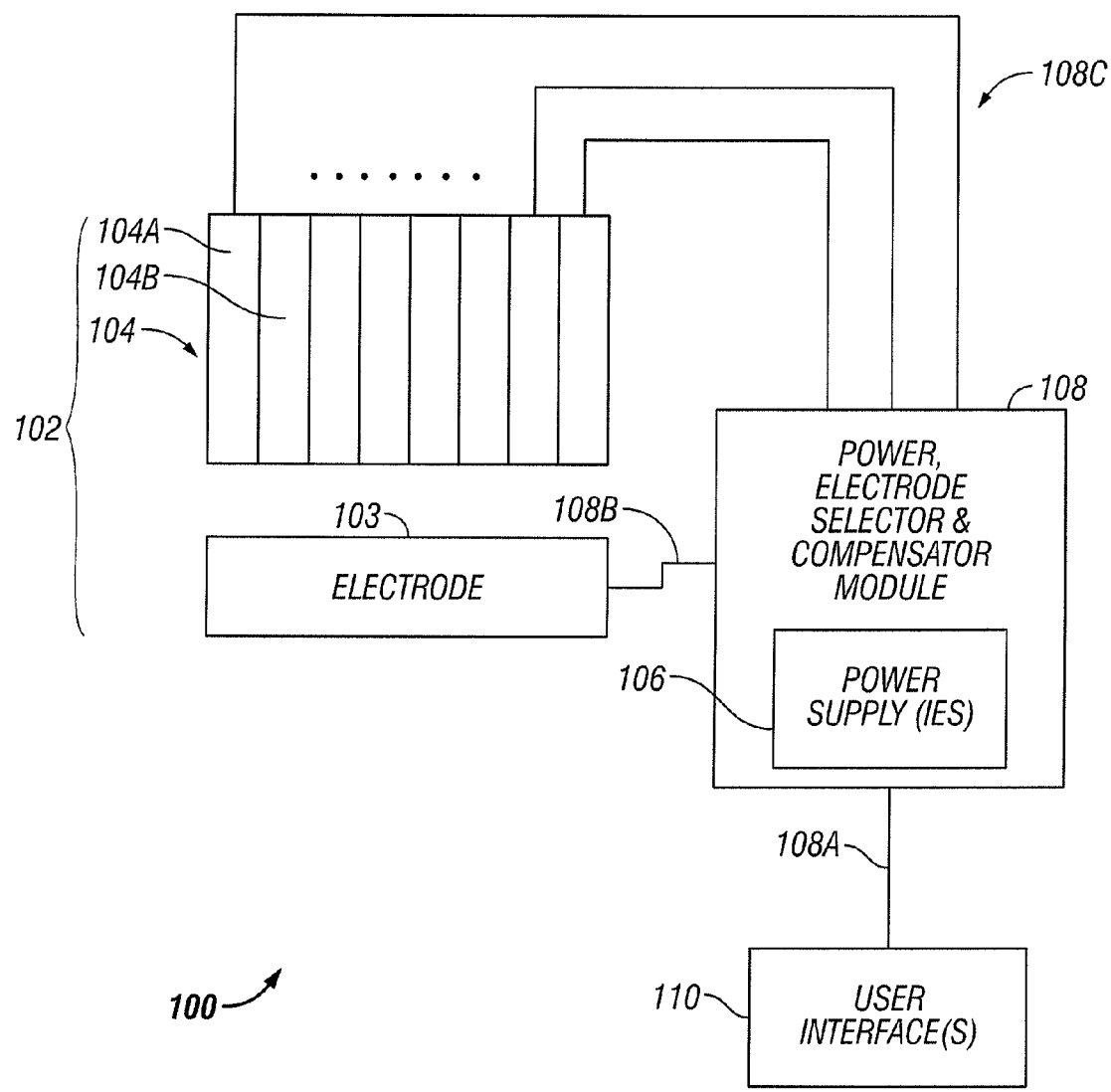
FIG. 1 is a block diagram of the components and interconnections of an electrocautery system according to the invention.

FIG. 1 illustrates one embodiment of electrocautery system 100. The system 100 includes an electrode structure 102 that is electrically driven by a power, electrode selector, and compensator module 108. The module 108 is operated in accordance with user input conveyed via one or more user interfaces 110.

As explained below in greater detail, certain components of the system 100 may be implemented with digital data processing features. These may be implemented in various forms.

Some examples include a general purpose processor, digital signal processor (DSP), application specific integrated circuit (ASIC), field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g. a combination of a DSP and a microprocessor, a plurality of microprocessors, one or more microprocessors in conjunction with a DSP core, or any other such configuration.

As a more specific example, a digital data processing includes a processor, such as a microprocessor, personal computer, workstation, controller, microcontroller, state machine, or other processing machine, coupled to digital data storage. In the present example, the storage includes a fast-access storage, as well as nonvolatile storage. The fast-access storage may be used, for example, to store the programming instructions executed by the processor. Storage may be implemented by various devices. Many alternatives are possible. For instance, one of the components may be eliminated. Furthermore, the storage may be provided on-board the processor, or even provided externally to the apparatus.

The apparatus also includes an input/output, such as a connector, line, bus, cable, buffer, electromagnetic link, antenna, IR port, transducer, network, modem, or other means for the processor to exchange data with other hardware external to the apparatus.

As mentioned above, various instances of digital data storage may be used, for example, to provide storage used by the system 100 (FIG. 1), to embody the storage, etc. Depending upon its application, this digital data storage may be used for various functions, such as storing data, or to store machine-readable instructions. These instructions may themselves aid in carrying out various processing functions, or they may serve to install a software program upon a computer, where such software program is then executable to perform other functions related to this disclosure.

An exemplary storage medium is coupled to a processor so the processor can read information from, and write information to, the storage medium. In the alternative, the storage medium may be integral to the processor. In another example, the processor and the storage medium may reside in an ASIC or other integrated circuit.

In contrast to storage media that contain machine-executable instructions (as described above), a different embodiment uses logic circuitry to implement processing data processing features of the system.

Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented with CMOS, TTL, VLSI, or another suitable construction. Other alternatives include a digital signal processing chip (DSP), discrete circuitry (such as resistors, capacitors, diodes, inductors, and transistors), field programmable gate array (FPGA), programmable logic array (PLA), programmable logic device (PLD), and the like.

Electrode Structure 102

Referring to FIG. 1, the electrode structure 102 includes first and second electrode surfaces 103-104. The electrode surface 104 is formed by a group of electrodes, such as individual electrodes 104a, 104b, etc. In one instance, the electrodes may be substantially contiguous. The electrode surface 103, in one instance, includes a single electrode, as illustrated. In another instance, the surface 103 includes multiple electrodes, of the same or different number than the electrodes 104.

In one embodiment the electrode surfaces 103-104 are arranged to provide electrical power to a targeted tissue area using opposed, bipolar electrodes. The use of opposed, bipolar electrodes is advantageous because it concentrates energy flux between the electrodes and limits the effect on adjacent tissue that is not confined within the opposed electrodes.

In one case, the electrode structures 103-104 may have generally similar geometries to contact tissue in a symmetric fashion. Alternatively, the electrode structures 103-104 may have dissimilar geometries. For example, one electrode structure may comprise a probe for insertion into a natural body orifice with the other electrode structure being structured to engage an exterior tissue surface apart from the body orifice. In some instances, more than two electrode structures may be employed, but at least two electrode structures, or separate regions of a single structure, are energized with opposite polarity to apply RF energy to the targeted tissue. In some instances, the electrode structures may be different regions formed as part of a single support structure, e.g. a single elastic tube or shell which may be placed over an organ or other tissue mass and which has two or more electrode surfaces formed thereon.

The different electrode surfaces are isolated from each other when high frequency energy of the same or opposite polarity is applied to them. In still other instances, a single electrode structure may have a plurality of electrically conductive or active regions, where the electrically conductive regions may be energized with the same or an opposite polarity.

In some instances, it may be desirable to provide additional structure or components on the electrode structures to enhance or increase the effective electrical contact area between the electrode structure and the tissue. In particular, the electrode structures may include tissue-penetrating elements to enhance electrical contact i.e. reduce electrical impedance between the electrode and the tissue and increase the total surface contact area between the electrode and the tissue. Exemplary tissue-penetrating elements include needles, pins, protrusions, channels, or the like. A particular example includes pins having sharpened distal tips so that they can penetrate through the tissue surface and into the underlying tissue mass. The pins may have depths in the range from 1 mm to 5 cm, or from 3 mm to 1 cm. The diameters of the pins range from 0.1 mm to 5 mm, or from 0.5 mm to 3 mm. In one instance, the pins are evenly distributed over the tissue-contact area of an electrode structure, with a pin density in the range from $0.1 \text{ pin/cm}^2$ to $10 \text{ pin/cm}^2$, or from $0.5 \text{ pin/cm}^2$ to $5 \text{ pin/cm}^2$. When tissue-penetrating elements are used, they may be dispersed in a general uniform matter over the electrically active area of the electrode structure. The pins or other tissue-penetrating elements may be provided in addition to an electrically conductive conformable or rigid electrode surface, but in some instances the pins may provide the total electrically conductive or active area of an electrode structure.

In one example, the electrodes comprise a plurality of different electrically conductive regions, where the regions may be electrically isolated from each other or may be electrically coupled to each other. Single electrode structures may include three, four, five, and as many as ten or more discrete electrically conductive regions thereon. Such electrically conductive regions may be defined by electrically insulating regions or structure between them.

One example of a multiple-electrode surface 104 is a plurality of electrically conductive strips that are separated by a gap which may be an air gap, a plastic member or other insulator. The gap is preferably less than 0.5 mm. In addition, multiple tissue-penetrating pins may be disposed along the length of each electrically conductive strips. The electrically conductive strips may be energized in an alternating polarity configuration. Most simply, opposing strips are connected to opposite polls on a single power supply. Electrical connections may be rearranged, however, to power the strips in virtually any pattern. Moreover, it is also possible to isolate different regions of each strip electrically to permit powering those regions at different polarities; or to set the electrodes to the same polarity but with various sequences of firing pattern that can include firing every electrode, firing specific electrode, or firing multiple electrodes simultaneously.

Although shown as flat plates, the electrode structure 102 may be implemented in a variety of different shapes without departing from the scope of the invention. For instance, the electrode structures 103-104 may be generally curved to facilitate placement over a tubular body structure or tissue mass. In one case, electrode configurations are specifically configured to have a geometry intended to engage a particular organ or tissue geometry. In other cases, the electrode configurations are conformable so that they can be engaged against and conform to widely differing tissue surfaces. In this regard, electrode strips may be constructed from such material as, for example, conformable meshes, permitting the electrode structures to be flattened out or to assume a wide variety of other configurations. Additionally, the insulating structures may also be formed from a flexible or conformable material, permitting further reconfiguration of the electrode structures. The structure 102 may be implemented according in any one, or a combination, of known shapes configurations, which are familiar to the ordinarily skilled artisan. Some exemplary shapes include opposing jaws, cylinder, probe, flat pads, etc. In this regard, the electrodes may be configured in any manner suitable for engaging a tissue surface.

Thus, the electrodes can be rigid, flexible, elastic, inelastic (non-distensible), planar, non-planar, or the like, and may optionally employ tissue-penetrating elements to enhance electrical contact between the electrode structure and the tissue, as well as to increase the electrode area. Electrode configurations may be conformable so that they can be engaged against and conform to widely differing tissue surfaces, or they are specifically configured to have a geometry intended to engage a particular organ or tissue geometry. In both instances, the electrode structures may further be provided with tissue-penetrating elements.

Optionally, electrode structures may include both a conductive surface and a non-conductive surface. In some embodiments this is accomplished by leaving one surface as an exposed metallic face, while the other surface of the electrode is covered or insulated with, for example, a dielectric material. In the case of rigid electrodes, the insulation can be laminated, coated, or otherwise applied directly to the opposed surface. In the case of flexible and elastic electrodes, the insulating layer is flexible so that it can be expanded and contracted together with the electrode without loss or removal. In some cases, a separate, expandable sheet of material covers the face for which insulation is desired. In some embodiments, all electrode surfaces may be coated with a dielectric material.

In one embodiment, the electrically active regions of the electrode structures have an area ranging from one to fifty $cm^2$ or larger. Further details and examples of electrode structures are explained in the U.S. patent applications as identified above as being incorporated herein by reference.

Power Supply 106

The power supply 106 includes one or multiple power supplies. Basically, the power supply 106 generates high frequency, such as RF, power for application to targeted tissue through one or more electrically active regions of the electrode structure 102. As described below, the duration and magnitude of power cauterizes or necroses tissue between the electrode surfaces 103-104.

Exemplary frequency bands include 100 kHz to 10 MHz or 200 kHz to 750 kHz. Power levels depend on the surface area and volume of tissue being treated, with some examples including a range from 10 W to 500 W, or 25 W to 250 W, or 50 W to 200 W. Power may be applied at a level of from 1 $W/cm^2$ to 500 $W/cm^2$, or 10 $W/cm^2$ to 100 $W/cm^2$, for example.

The power supply 106 may be implemented using various conventional general purpose electrosurgical power supplies. The power supply 106 may employ sinusoidal or non-sinusoidal wave forms and may operate with fixed or controlled power levels. Suitable power supplies are available from commercial suppliers.

In one embodiment, the power supply provides a constant output power, with variable voltage and current, where power output varies based upon load. Thus, if the system sees a very high impedance load, the voltage is maintained at a reasonable level to avoid arcing. With tissue electrocautery, impedance ranges from two ohms to 1000 ohms, for example. By applying constant power, the power supply 106 can provide significant current at low impedance to achieve initial desiccation when the tissue is first being cauterized and, as cauterization proceeds, to apply higher voltage to complete the tissue sealing process. Thus, the power supply 106 can provide larger current and smaller voltage at the beginning of the cauterization process and a higher voltage and lower current at the sealing phase of the process. Control of such power generator is based, at least in part, on the system 100 monitoring power.

In one embodiment, the power supply 106 includes a mechanism for setting the desired power. This setting may occur by real-time control, pre-set selection by a user, default settings, selection of predetermined profile, etc. In one embodiment, pulse width modulation is used in connection with a flyback transformer. The system charges a primary of the flyback transformer and produces a regulated output. The secondary may be regulated, for example, to 15 volts at a desired number of amperes to produce the desired power output. Based upon the period, as determined by the width of the pulse which charges the primary, the power curve is determined. Thus, the invention establishes a certain level of power in the primary of the flyback transformer and the same level of power is provided by the secondary without regard to impedance of the load, i.e. the tissue.

The power supply 106 may include digital data processing equipment, such as mentioned above. This optional equipment, if implemented, is used to establish and control features and operation of the power supply 106.

As illustrated, the power supply 106 is a source of power for multiple electrodes of the structure 102. Accordingly, the power supply 106, or the module 108, provides multiple output channels, each of which is independently adjustable. In this embodiment, the system 100 includes a conductive supply path of multiple conductors 108c to provide power to the electrodes, and a return path 108b for providing a ground path and/or feedback to the power supply or vice versa, depending on the direction of current flow.

In a more particular embodiment, the module 108 has multiple outputs 108c routed to the individual electrodes by a digital data processor of the module 108. These multiple outputs are independently operated by the processor and readily modulated and assignable. Thus, the processor may assign an output to any one or more of the electrode elements at a certain point in operation of a cauterization cycle, and dynamically reassign them other points of time. For example, if the power source were a four channel power source and the electro-surgical device had sixteen electrodes, then each channel may support four electrodes in electro-surgical device. However, this arrangement may be varied so that some channels support more electrodes than others.

Figure 2:
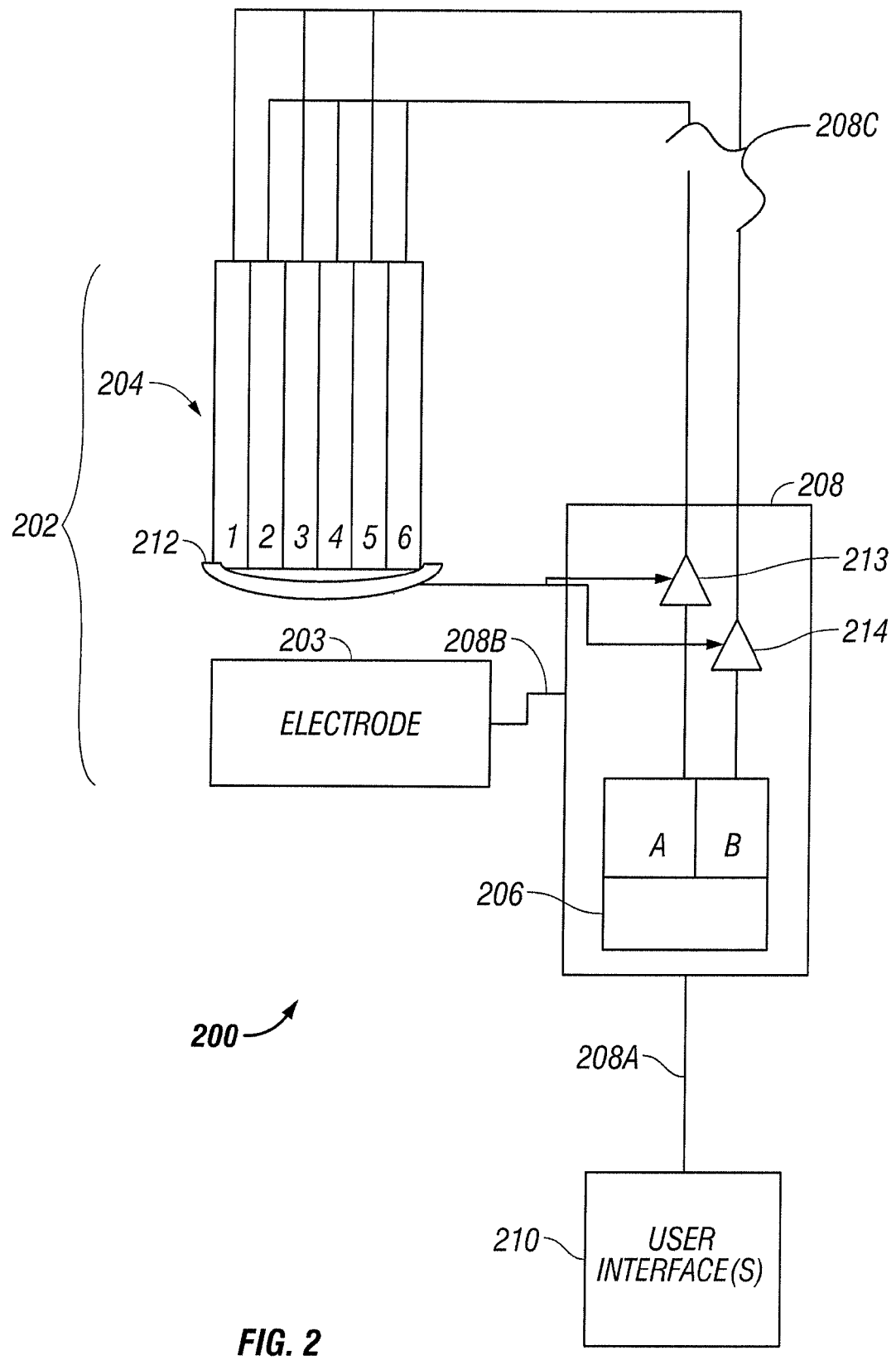
FIG. 2 is a block schematic diagram of an electrocautery apparatus having a multi-channel power supply according to the invention.

Referring to FIG. 2, an electrode structure 202 includes first and second electrode surfaces 203-204. The electrode surface 204 is formed by a group of electrodes which comprise individual electrodes 1-6. The specific configuration of the electrodes 1-6 and electrodes 204 may be provided as discussed herein above. Significant to this embodiment in the invention is that each of the electrodes is individually addressable. Further, while a single return electrode 203 is shown, those skilled in the art will appreciate that multiple electrodes may be provided for both electrode surface 204 and electrode surface 203. Electrode surface 203 is shown coupled to a module 208 by conductors 208B. Likewise, the array of electrodes 1-6 and electrode surface 204 are coupled to the module 206 by conductors 208C. Significant to this embodiment of the invention is that the module 208 includes a power supply 206 having multiple channels. In this embodiment of the invention channels A and B are shown. Those skilled in the art will appreciate that any number of channels may be provided for power supply 206 and that the example herein provided is provided for purposes of explaining the invention and not by way of limiting the invention.

As with the embodiment of FIG. 1, a user interface 210 is coupled to the module 208 by a connector 208A. Thus, FIG. 2 shows an entire electrocautery apparatus 200. Also shown in FIG. 2 is a sensor array 212, which is used to control the output of each of power supply channels A and B through a control mechanism 213/214. The sensors are discussed in greater detail below. The actual frequency bands and power levels, etc. of the power supply 206 may be selected in accordance with the discussion above of power supply 106 (FIG. 1).

Key to this embodiment invention is the fact that the power supply is operable to power up to adjacent electrodes simultaneously. Thus, upon actuation of the device, power supply channels A and B can provide power through connections 208C to one more of the respective electrode elements 1-6. For example, upon initiation of device operation, power is provided from channel A of power supply 206 to electrode 2, while power is provided from power supply 206 channel B to electrode 1. Thus, adjacent to electrodes 1 and 2 are powered simultaneously.

In this embodiment, while a single line is shown for each channel leading from the power supply to the electrocautery device, those skilled in the art will appreciate that each element in the array is individually addressable by the power supply in some embodiments of the invention. Thus, channels A and B may be powered-up to fire electrodes 1 and 2 and, thereafter, electrodes 3 and 4 can be fired, and thereafter electrodes 5 and 6 can be fired. In other embodiments of the invention it is not necessary to fire the electrodes together and each channel may be fired individually. However, one key aspect of this embodiment is the ability to fire electrode paired sequentially.

In an electrocautery device in which the electrode array 204 is provided along the extent of a clamping surface of an electrocautery device, such that electrodes 1 and 2 are at a proximal end of the device and electrodes 5 and 6 are at a distal end thereof, then such arrangement allows the electrodes to be fired in sequential fashion, proximally to distally or otherwise. For example, electrode pairs 3 and 4 may not be covering tissue while electrode pairs 5 and 6 do cover tissue. In this example, the sensors notify the power supply not to fire electrodes 3 and 4 during a sequential firing sequence. For example, electrodes 1-6 are fired in sequence, but during the sequence no power is provided to electrodes 3-4. Essentially, the sensors determine that processing of tissue has proceeded more rapidly along portions of the clamping surface of the electrocautery device. As such, the power supply may be modulated such that more power is provided as appropriate for the progress of tissue processing along a processing extent. For example, less or no power is provided to electrodes 3-4, while more power is provided to electrodes 5-6, for example, because the tissue is not yet fully processed these locations. Thus, the invention allows the processing of tissue along an extent of tissue, where the actual power applied for processing is modulated in accordance with the conditions of the tissue. In this way, the tissue is evenly processed and not overprocessed.

In other aspects of the invention in this embodiment is that the cycle time of the device is optimized. Because two electrodes are charged simultaneously, for example, where there are two channels to the power supply, the device is able to deliver energy to the tissue at two locations simultaneously. Thus, in the example FIG. 2, electrodes 1 and 2 are charged and fired simultaneously. In this way, the system does not have to charge for each individual electrode, but rather the time needed to charge for electrodes is effectively cut in half because each channel is responsible for each alternate electrode. While six electrode surfaces are shown in FIG. 2, those skilled in the art will appreciate that any number of electrodes may be provided. Further, while the discussion herein describes electrode firing as occurring in adjacent pairs in a proximal to distal sequence, any combination of electrode firing may be affected. For example, channel A may fire electrodes proximally to distally, while channel B may simultaneously fire electrodes distally to proximally, etc.

User Interface 110

The user interface 110 comprises one or more devices for a human to exchange information with the module 108, including the power supply 106. There may be a common user interface, or separate user interfaces for each component 106, 108.

The user interface may be implemented in various ways, with the following serving as some examples. As for human-to-machine flow, some examples of the interface 110 include buttons, dials, switches, keyboards, remote control console, or other mechanical devices. Other examples include pointing devices such as a mouse, trackball, etc. Still other examples include digitizing pads, touch screens, voice input, or any other example suitable for the purposes described herein. As for the machine-to-human exchange, the interface 110 may employ a video monitor, display screen, LEDs, mechanical indicators, audio system, or other example suitable for the purposes described herein.

User input is conveyed from the interface to the module 108 via the link 108a.

Sensors

The system 100 may also include various sensors attached to various components of the system 100. The sensors, which are not shown in FIG. 1 to avoid cluttering the diagram, may be attached to components such as the electrodes 103-104, subparts of the module 108, equipment of the power supply 106, and the like. Examples of these sensors include devices for sensing voltage, current, impedance, phase angle between applied voltage and current, temperature, energy, frequency, etc. More particular, some of these devices include voltmeters, analog-to-digital converters, thermistors, transducers, ammeters, etc. Thus, measurements may be made of any of the above parameters, either alone or in combination. Further, such measurements may yield either or both of real-time (instantaneous) values or values that represent change in one or more parameters over time. In this way, for example, such factors as thresholds, trends, etc. may be detected and used to establish and control a power output profile for the power supply. As discussed above, such power profile may be applied for individual electrodes, groups of electrodes, on a channel-by-channel basis, or any combination thereof.

Module 108

As shown above, the module 108 includes one or more power supplies 106. Aside from this function, module 108 may be implemented to perform some or all of automated or user-selected operation or compensation of the electrodes in the manner shown below. According to one aspect, the module 108 may be used to target a specific region of tissue, or the control firing order of electrodes, by selectively limiting power application to electrodes whose selection is predetermined, machine-selected, or user-selected. According to another aspect, the module 108 may introduce impedance into the electrode circuitry to provide a predetermined, machine-selected, or user-selected impedance matching or compensation. According to one optional aspect of the module 108, the module 108 may target a specific region of tissue by selectively limiting power application to electrodes whose selection is predetermined, machine-selected, or user-selected. In this regard, the module 108 has a variety of outputs 108b-108c individually coupled to each of the electrodes 103-104. As one example, the outputs 108b-108c may comprise wires, cables, busses, or other electrical conductors. In the illustrated example, there are multiple conductors 108c leading to the multiple electrodes 104a, 104b, etc.

The module 108 applies voltage from the power supply 106 across the first and second electrode surfaces 103-104, such that the voltage is applied exclusively to selected ones of the electrodes. These electrodes may be selected according to user input from the interface 110, selected by a machine-implemented analysis, and/or selected by a default state. In this regard, the module 108 may include a switching network of electrical and/or mechanical switches, relays, or other mechanism to provide power to selected ones of the electrodes. As shown, the power supply 106 is integrated into the module 108, and computer control selectively activates selected output conductors.

Whether by independent switching network or computer regulated activation of output conductors, the module 108 activates electrodes according to input from user interface 110, or input from a machine such as a digital data processing device as discussed above. Depending upon the nature of the application, such controlled application of power to electrodes may be performed in accordance with a machine-selected criteria or analysis, default state, or user input.

Figure 3:
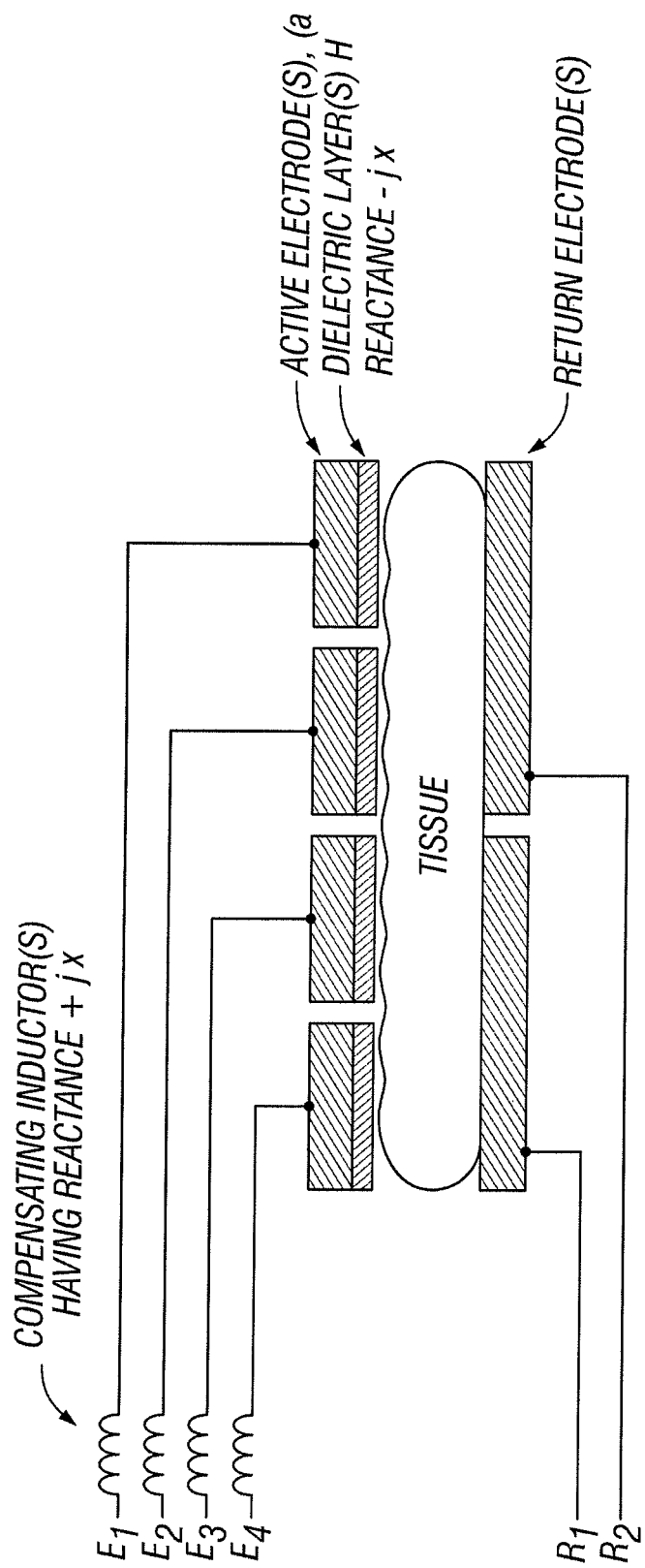
FIG. 3 is a combination block and schematic diagram illustrating an electrocautery device with circuitry for selectively firing electrodes according to the invention.

FIG. 3 illustrates a typical application of one example of a processor-controlled switching network, shown in context of two power supplies, electrode structures, and a targeted tissue region. In this example, the electrode surfaces are configured as follows. The electrode surfaces are substantially parallel during performance of electrocautery, each electrode of one surface is aligned with its counterpart in the other electrode surface. In this example, there are two electrodes from the upper surface corresponding to each electrode of the lower surface.

Significantly, the module 108 selectively limits power application to certain electrodes, to target a specific region of tissue. Electrodes may be selected for a different end, as well. Namely, the module 108 may monitor or control the selection of electrodes to prevent firing of adjacent electrodes of the same electrode surface concurrently or sequentially. Ensuring that electrode firing occurs in this spaced-apart fashion prevents unintentional arcing between electrodes and improves the effectiveness of electrocautery. In one embodiment, the controlled firing order is implemented by computer control, and particularly, by a digital data processing component of the module 108. As an alternative to computer control, mechanical means may be used, such as an electromechanical distributor or other device.

In another embodiment, the module 108 may introduce impedance into the electrode circuitry to provide predetermined, machine-selected, fixed, or user-selected impedance matching or compensation. In other words, the module 108 contains a mechanism to electrically introduce impedance into a circuit containing the power supply, the outputs 108b-108c, and the electrodes 103-104.

More particularly, the module 108 includes capacitors, inductors, and/or other impedance elements that can be adjusted or selectively introduced to control the amount of impedance in the circuit containing the power supply and electrodes 103-104. These impedance elements may comprise discrete elements, integrated circuit features, or other constructs suitable for the purposes described herein. The module 108 establishes this impedance matching or compensation according to directions from a user, machine-implemented analysis, and/or default setting.

One example of an adjustable impedance is an adjustable inductor that may comprise any known inductance, such as a coil of conducting material wrapped around an adjustable ferromagnetic core or discrete inductors. In this example, the overall inductance is selectively increased by closing a switch that may be activated manually, mechanically, electrically, or by any means suitable to the purposes of this disclosure, for example, via the user interface 110.

Figure 4:
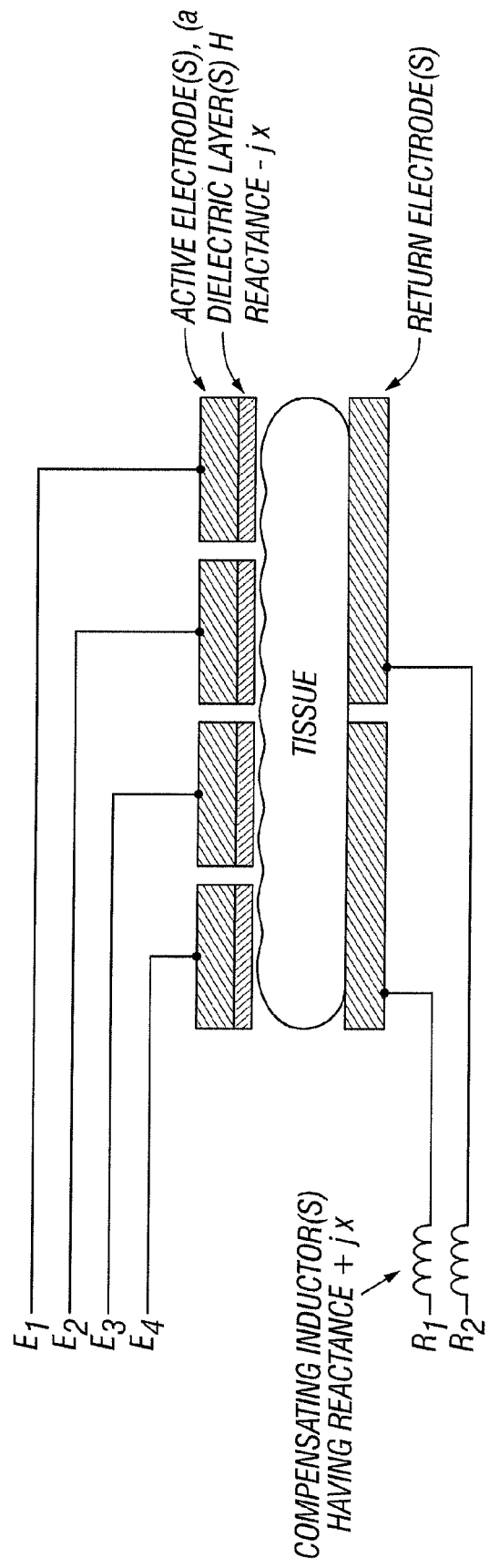
FIG. 4 is a combination block and schematic diagram illustrating an electrocautery device with a first embodiment of compensating circuitry according to the invention.

FIG. 3 illustrates an electrode arrangement having an inductance in series with each electrode of an upper electrode surface (as illustrated). FIG. 4 shows a different example, including an inductance in series with each electrode of the lower electrode surface (as illustrated). In a different example still, FIG. 5 contains "T" type network where a capacitor is placed in series with each electrode of the upper electrode surface. Additionally, a different inductor is placed in parallel with each pair of electrodes that are designed to be activated together. The examples of FIGS. 3-5 may employ impedance elements that are fixed, adjustable, or a combination of fixed and adjustable. Furthermore, in connection with the electrodes having a dielectric coating on their surface, a nearly limitless number of additional circuitry configurations for impedance matching and/or compensation will be apparent to ordinarily skilled artisans having the benefit of this disclosure.

Figure 5:
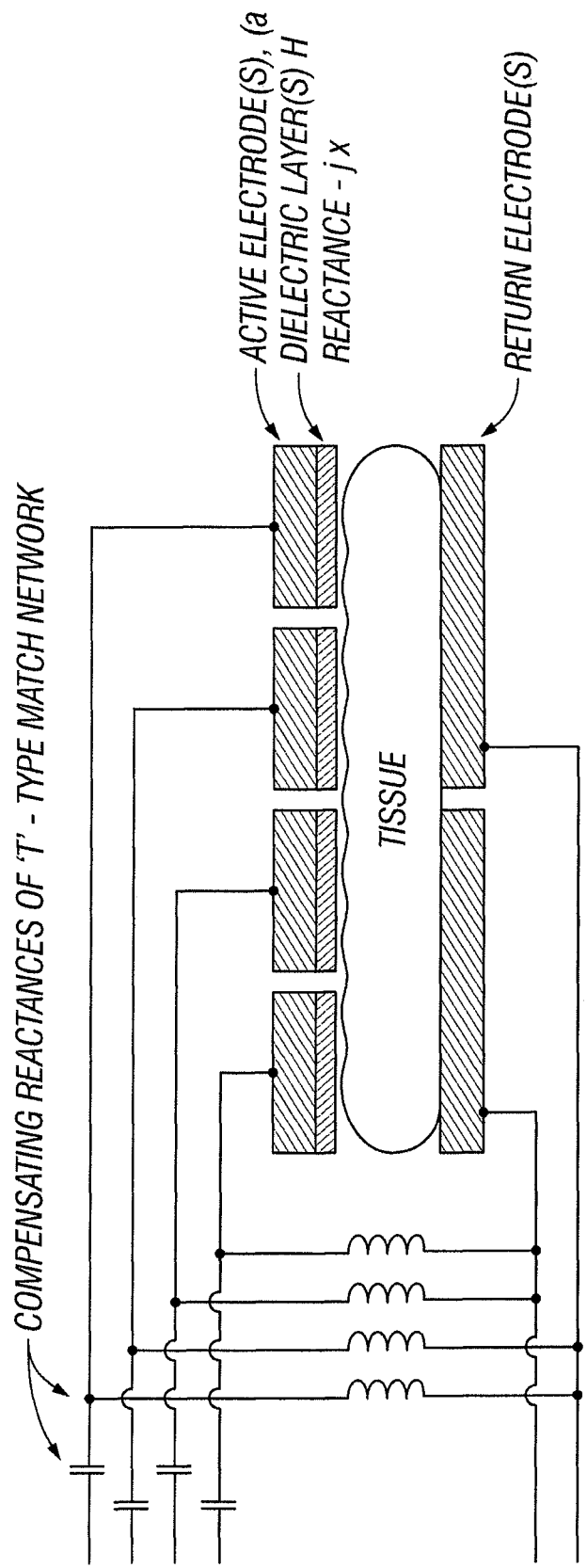
FIG. 5 is a combination block and schematic diagram illustrating an electrocautery device with a second embodiment of compensating circuitry according to this invention.

In addition to the arrangement for introducing impedance into the electrode circuits, another consideration is the value of such impedance elements. In one example, the impedance is selected to achieve maximum power transfer and to make accurate power measurements. In this regard, the impedance is chosen to maintain an impedance match between the RF generator, namely, the power supply 106, and the tissue. Impedance matching is achieved when the phase-angle between applied voltage and current is zero. Namely, additional inductance is increased to compensate for the increased capacitive reactance. In one example, this is carried out with a continuously variable inductor, with a finite range and nearly infinite resolution. Such an inductor can be adjusted to a near zero phase. In a different example, impedance matching is carried out by using discrete inductive elements in an appropriate arrangement, such as shown in FIGS. 3-5, to find the least possible phase angle, though this may not be exactly zero.

Having described the structural features of the invention, the operational aspects of the invention will be described. The steps of any method, process, or algorithm described in connection with the embodiments disclosed herein may be embodied directly in hardware, in a software module executed by hardware, human-performed steps, or a combination of these.

A sequence for performing an electrocautery procedure uses an electrocautery system that includes an electrode structure and a mechanism for automated or user-selected operation or compensation of the electrodes. For ease of explanation, but without any intended limitation, this example is described in the specific context of the system 100 of FIG. 1.

In a first step, different parameters for operating the system 100 are selected. In one example, one or more human users select these parameters and convey them to the system 100 via the user interface 110. In a different example, the parameters for operating the system 100 are selected by digital data processing equipment aboard the module 108. In this case, the parameters are set according to user input, default values, measurements gathered by the various sensors installed in the system 102, programming of the module 108, etc.

Without any intended limitation, the following are some non-exclusive examples of parameters that may be selected in the first step:

(1) Identity of individual electrodes to be activated e.g., FIG. 3 to focus energy of the electrodes 103-104 on a specific region of tissue.

(2) Firing order of electrodes.

Figure 6:
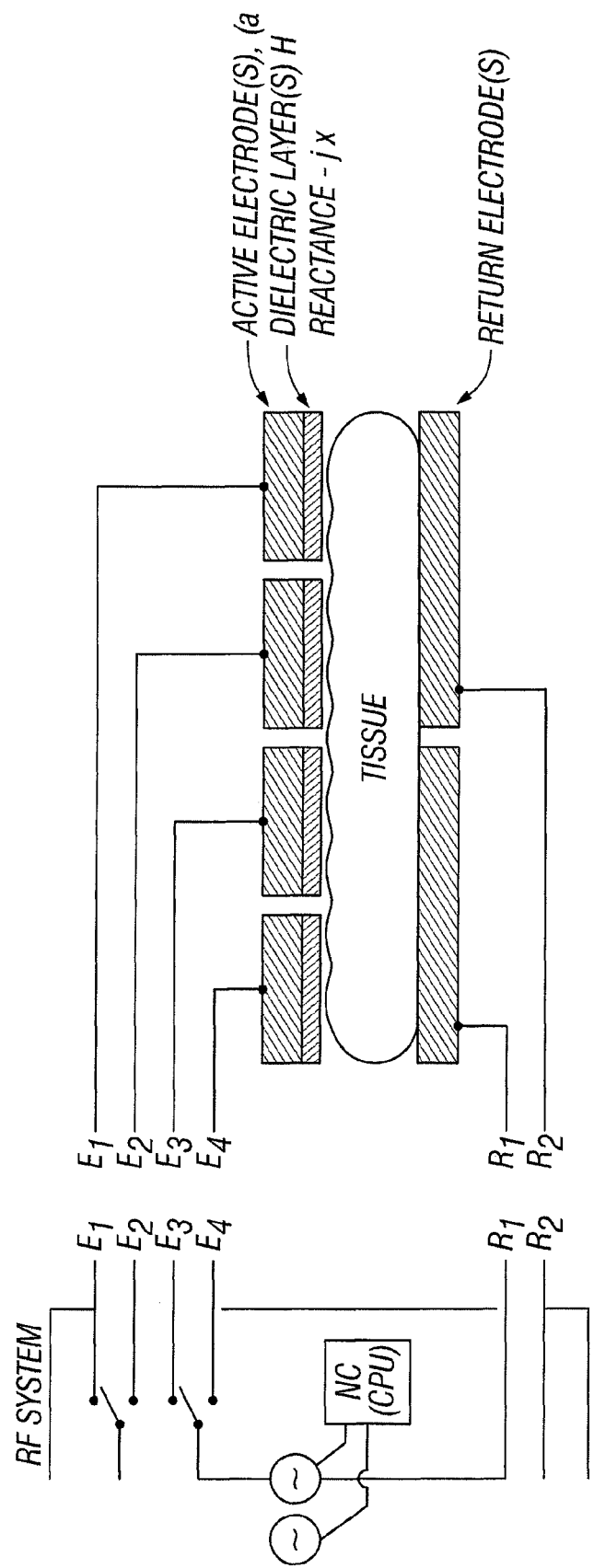
FIG. 6 is a combination block and schematic diagram illustrating an electrocautery device with a third embodiment of compensating circuitry according to the invention.

(3) Assessment or measurement of magnitude of impedance, e.g. FIGS. 4-6, to be used in compensating and/or impedance matching between the power supply 106 and electrodes 103-104.

(4) Parameters of electrical power to be applied in electrocautery, such as magnitude, frequency, phase, or other characteristics of voltage, current, power, etc.

(5) Any other parameter by which the operation of the system 100 can be varied.

In a next step appropriately trained personnel apply the electrodes 103-104 to a targeted tissue region to be electrocauterized. The manner of applying the electrodes 103-104, varies according to the construction of the electrodes 103-104, the nature of the targeted body part, the procedure to be performed, and other such factors. There may be circumstances where both electrode structures 103-104 are used within the body, and other embodiments where one electrode is inserted into the body and the other electrode used externally, i.e. bipolar or monopolar applications, as is know in the art.

In a specific example of this next step, there are multiple electrodes of one surface, such as 104, corresponding to one electrode of the other surface, such as 103. Optionally, personnel arrange the first and second electrode surfaces 103-104 so that the electrode surfaces are substantially parallel, and each one of the second electrodes is aligned with its corresponding first electrodes, although alignment is preferably obtained during manufacture of the device. FIGS. 3-6 show examples of the final arrangement.

In a further step, directions are given to begin electrocautery. This occurs by user input submitted via the interface 110. For example, a user may press a start button, utter a start command, press a foot pedal, trip a lever, or perform other action. In a different example, electronically occurs upon expiration of a user-initiated timer.

In a still further step, the system 100 responds to the start command and electrocautery is conducted. Here, the system 100 directs bipolar RF power at target tissue regions defined by spaced-apart placement of the electrode structures 103-104. The use of opposed, bipolar electrodes concentrates energy between the electrodes and limits the effect on adjacent tissue that is not confined within the opposed electrodes. In practice, power may be applied for a time sufficient to raise the tissue temperature in the tissue mass being treated to above a threshold level required for cauterization or necrosis, such as 60-80° C., or even higher.

More specifically, electrocautery is conducted according to the configuration set. For instance, the power supply 106 operates according to the power settings established. Moreover, the module 108 acts to invoke individual ones of the electrodes according to the electrode combination selected. In other words, the module 108 applies voltage from the power supply 106 across the first and second electrode surfaces 103-104, such that voltage is applied exclusively to the electrodes selected in. In the case of computer control, this is achieved by the module 108 selectively applying power to the selected electrodes.

As a further enhancement to the use of selected electrodes, the electrodes may be activated using a selected firing order. In this example, the module 108 applies voltage from the power supply 106 across the first and second electrode surfaces 103-104, such that voltage is applied to one or more of the first electrodes 102 and one or more of the second electrodes 103 at any one time, and the module 108 prevents firing of adjacent electrodes of the same electrode surface concurrently or sequentially. The module 108 may further implement a predetermined or user-selected firing order.

For example, one way of preventing interaction, either thermal or electrical, between two or more multiple electrodes in an RF device with multiple electrodes is to alter the firing sequence of electrodes so that adjacent electrodes are never sequentially charged. For example, instead of sequential firing a four electrode system, where the electrodes are sequentially numbered 1,2,3,4, the invention fires them in an order such as 3,1,4,2, 4,2, 4,1,3,1,3, etc. so that adjacent electrodes are not fired sequentially. Firing times may be different for each electrode to balance the energy delivered in such a sequence where some electrodes fire more frequently than others. This prevents cross-talk during the transmission from one electrode to another as well as cumulative effects of sequential heat build-up in the transition area between the two electrodes. Additionally, rounded electrodes can minimize the edge effect that occurs between electrodes and at any transition surface.

Additionally, if one electrode surface or both opposing surface of conductive, typically metal, electrodes are coated with dielectric, non-conductive materials, RF energy may still be transmitted through tissue between them via capacitive coupling. FIG. 6 is a block diagram showing an electrode having a dielectric coating according to the invention. However, due to the non-conductive nature of the surface coating the electrode surfaces does not create a short circuit if brought into close proximity or contact. In this way, if a portion of an electrode pair only partially captures tissue, i.e. there is a small, 5 mm air gap between a portion of the electrodes, the RF energy still passes through the tissue, as opposed to going around the tissue and flowing directly between the close proximity electrodes. This is especially important late in the sealing cycle as the tissue impedance rises. When the tissue impedance is high the energy seeks alternate pathways of lower resistance, such as between exposed electrode sections. These dielectric layers can be thin coats of polymers, such as Teflon, metal oxides, such as titanium, tungsten, or tantalum or ceramics. To obtain adequate capacitance these layers may be in the micron range of thickness.

In an alternative embodiment, a variety of different tissue cauterization patterns can be achieved with the system 100 by selectively energizing different ones of the electrode surfaces or regions. By selectively energizing two adjacent electrodes, while leaving all other electrodes non-energized, a limited tissue region is cauterized. In contrast, by energizing other multiple electrode surfaces, a larger region is cauterized. Slightly different patterns are achieved depending on the precise pattern of electrode surface polarity. In other embodiments, the electrode surfaces can be energized in an alternating pattern of polarity to produce a tissue cauterization pattern. Different patterns may also be used to produce somewhat different patterns of cauterized tissue.

A different approach for selected firing is employed to prevent local areas of high impedance from impacting the overall system impedance along the entire electrode, and thus potentially reducing the power output of the entire system as voltage reaches its maximal capacity. Here, electrodes are activated to prevent one area that has already been well sealed and has thus reached high impedance value from affecting other regions in which the tissue is not yet sealed, and is thus at a lower impedance. Optionally, the module 108 may employ unique power and energy delivery profiles for each electrode or electrode pair, based on the properties of the tissue in a specific electrode location/position.

The performance of electrocautery employs the selected impedance compensation and/or matching selected. As a result, power delivered from the power supply 106 is delivered to the targeted tissue region with less electrical loss.

The system 100 may further sense and automatically adjust conjugate matching impedance. In response, the module 108 adjusts the impedance applied to the conductive path containing the electrode surfaces 103-104 and power supply 106. Alternatively, the sensors may provide raw data to the module 108, which analyzes whether and how to adjust impedance. In a different instance, the module 108 may adjust impedance responsive to direction or data from the sensors. This can be carried out by changing the frequency of RF energy delivered by the power supply 106. For example, in one embodiment the module 108 senses whether or not tissue is present at each electrode at the beginning of a cauterization cycle by measuring any of impedance, pressure, or any combination of these and/or other parameters. If tissue is not present at any electrode, then such electrode pair is idle; the module 108 deactivates firing of this electrode, and/or provides a warning to an operator via the user interface 110. The module 108 may also provide a status indicator for each electrode pair that indicates whether the sealing cycle is active or completed with regard to each electrode pair. In this embodiment, each electrode pair may include a mode status indicator, such as an LED for example, that indicates any of an idle, active, or complete condition, once a cauterization cycle is commenced.

Figure 7:
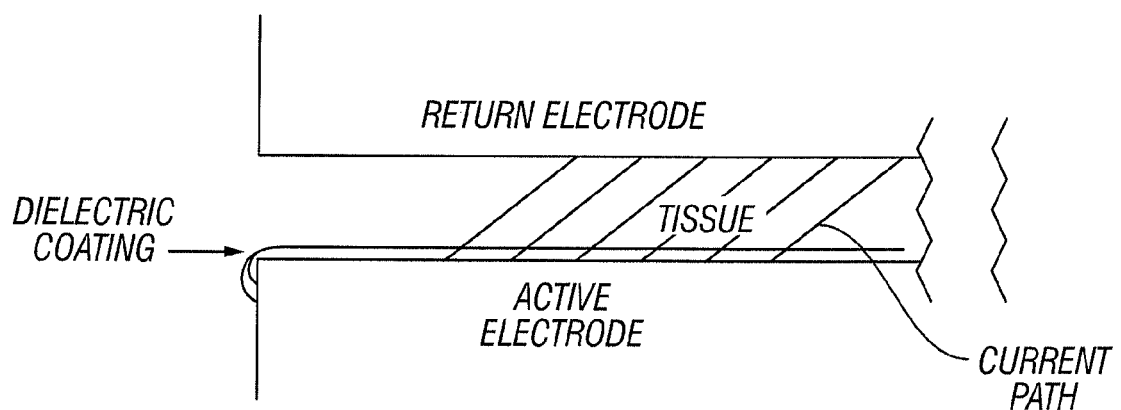
FIG. 7 is a block diagram showing an electrode having a dielectric coating according to the invention.

The invention also addresses the problem of determining the area of tissue coverage of one or more electrodes through the use of dielectric coated electrode surfaces (See FIG. 7). With a suitable RF generator and with electrode surfaces coated with a dielectric coating, determination of tissue coverage may be obtained by measuring phase-angle of RF voltage and current. Because a dielectric coating essentially forms a capacitive coupling to tissue, for a given dielectric material thickness, the capacitance is a function of the area of coverage.

The basic formula for a capacitor is:

$$C = \epsilon_0 \epsilon_r A/d$$

Expressed in Farads, where so is the permittivity of free-space (8.854E-12), $\epsilon_r$, is the relative permittivity of the dielectric, A/d is the ratio of the area and the dielectric thickness.

At a given frequency, the reactance is expressed as $$Xc = 1/\omega C$$

where $\omega$ is 2*Pi*Frequency.

A suitable RF generator is required to insert a conjugate impedance inductance in this case to cancel out the capacitive reactance with a fully covered electrode and to measure the phase-angle of RF voltage and current. When an electrode is only partially covered, the capacitance changes i.e. becomes smaller, because the effective area is smaller. As a result, the reactance and, ultimately, the phase-angle of RF voltage and current change. While the magnitude of change is affected in part by the tissue resistance, it is believed that this methodology allows the greatest degree of determination of electrode coverage by tissue.

A further advantage of such a methodology may signal the RF generator's control algorithm to change frequency, e.g.

increase, with smaller surface areas, thus maintaining maximum power transfer while minimizing chances for electrical arcing and tissue charring. Potential electrical arcing and tissue charring conditions may be detected rapidly by rapid changes in phase and/or impedance and by appreciating that electrodes which are only partially covered by tissue may be used to signal the RF generator control algorithm to shorten or change treatment parameters.

To achieve maximum power transfer and to make accurate power measurements, it is desirable to maintain an impedance match between the RF generator and the tissue. Impedance matching is achieved when the phase-angle is zero. Several methodologies may be used to attain near-zero phase. One such methodology uses additional reactive elements e.g. greater inductance, to compensate for the increased capacitive reactance. This approach can be achieved in two different ways:

(1) Via the insertion of a continuously variable inductor with a finite range and nearly infinite resolution, such an inductor can be adjusted to a near zero phase; or
(2) Via the insertion of discrete elements, e.g. inductors to find the lowest phase, though this may not be near-zero phase.

In both cases, electro-mechanical devices are required within the RF generator.

Another methodology of achieving maximum power-transfer, e.g. zero phase, is by changing the RF frequency. Given that the reactance is frequency dependent, this methodology allows the RF generator to compensate for phase discrepancy by electronically changing frequency. This may not require any mechanical devices such as relays, servos, etc. Further, the RF generator can change frequency during operation rather than first interrupting RF power to change elements. Thus, this may be the most desirable methodology.

Figure 8:
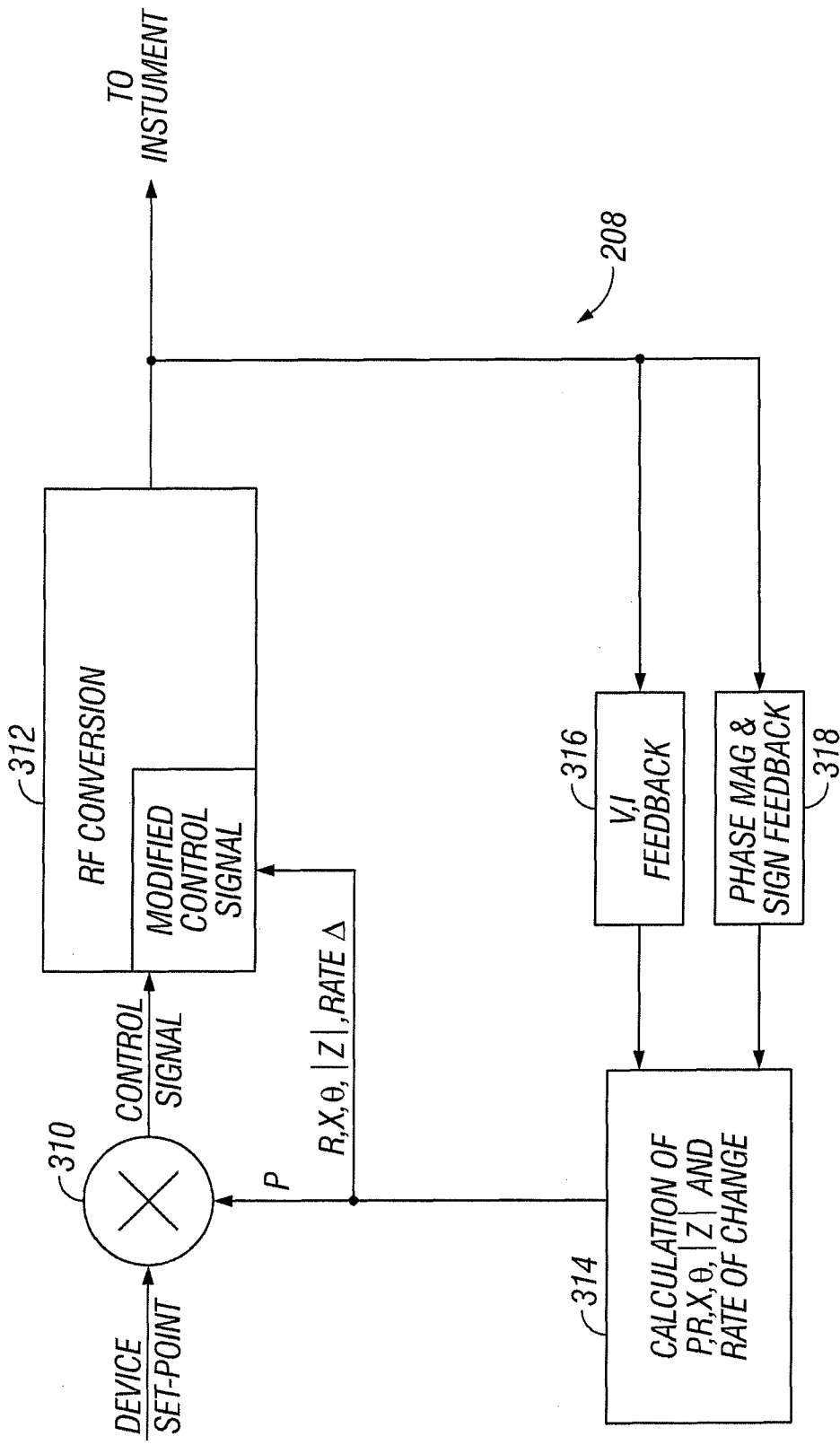
FIG. 8 is a block schematic diagram showing the module 208, as in FIG. 2, but in greater detail and in particular showing the control circuit thereof.

FIG. 8 is a block schematic diagram of the module 208 shown in FIG. 2, showing in more detail the control circuitry. A user determined device set-point is provided to a control circuit 310. The control circuit 310 receives both the set-point information and also calculation of such parameters as power, resistance, phase, impedance, and the like, as well as rate of change of such parameters, from a calculation module 314. A control signal is provided to an RF conversion circuit 312 which then produces an out-put signal that is provided to the electrodes in the instrument. The rate of change information is also used to produce the modified control signal. In this way, feedback from the instrument received in the form of voltage and current through a detection system 316 and phase magnitude and sign feed-back received through a phase magnitude and sign feedback circuit 318 are provided to the calculation circuit 314 to produce a rate of change signal that is used to modify the control signal.

In accordance with the foregoing description provided, in connection with FIG. 8, those skilled in the art will appreciate that the circuit in FIG. 8 is that of a single channel. As discussed above, the invention herein comprises a power supply that provides multiple channels. The various configurations and electrodes are discussed above. The invention allows control of electrodes, for example, adjacent electrodes on the same side of a device jaw, or on opposite sides of a device jaw.

Further, the electrodes may be parallel to each other and/or opposite each other, and may be activated simultaneously by separate channels or may be subjected to sequential operation of the electrodes through controlled operation of the separate power supply channels. Combinations of the foregoing is also possible. An exemplary embodiment of the invention comprised a unique power generator for each electrode or group of electrodes. This allows for independent control of electrodes in connection with instruments that employ more than one electrode.

Key to the invention is the provision of multiple channels which independently power respective electrodes in an instrument. Of further importance, is the ability to monitor factors such as voltage, current, impedance, phase angle between applied voltage and current, temperature, energy, frequency, and combinations thereof with sensors provided in or associated with an instrument such that an instantaneous signal and/or a signal representing change over time of one or more of these parameters is used to control the power supply output on a channel-by-channel basis. In this way, cauterization across a large cross section of tissue is effected in a way that takes into account the disparity of tissue thickness in the tissue cross section.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. A bipolar electrocautery apparatus, comprising:
a plurality of opposed bipolar electrode pairs comprising a plurality of first electrodes forming a first electrode array and one or more second electrodes;
a power supply electrically coupled to at least one opposed bipolar electrode pair of the plurality of opposed bipolar electrode pairs; and
a compensator module comprising:
one or more feedback devices configured to detect a voltage, a current, a phase magnitude, and a phase sign of energy supplied to the at least one opposed bipolar electrode pair by the power supply;
a calculation module configured to calculate a power, a phase, and an impedance based on the voltage, current, phase magnitude, and phase sign in order to sense an amount of tissue coverage between the at least one opposed bipolar electrode pair; and
a control circuit configured to generate a control signal for controlling the supply energy supplied to the at least one opposed bipolar electrode pair by the power supply based on user-determined set-point information and the calculated power, phase, and impedance from the calculation module, the control signal generated by the control circuit operable to adjust the impedance by changing a frequency of the energy supplied by the power supply across the at least one opposed bipolar electrode pair in response to sensing that the amount of tissue coverage between the at least one opposed bipolar electrode pair is less than a full amount of coverage possible for the at least one opposed bipolar electrode pair.

2. The bipolar electrocautery apparatus of claim 1, wherein the compensator module is operable such that if it is sensed that the amount of tissue coverage is zero between the at least one opposed bipolar electrode pair, the compensator module deactivates the at least one opposed bipolar electrode pair.

3. The bipolar electrocautery apparatus of claim 1, wherein the at least one opposed bipolar electrode pair comprises at least two or more opposed bipolar electrode pairs of the plurality of opposed bipolar electrode pairs, the at least two or more opposed bipolar electrode pairs being adjacent to one another, and wherein the compensator module is operable such that it is able to fire the at least two or more opposed bipolar electrode pairs that are adjacent to one another concurrently.

4. The bipolar electrocautery apparatus of claim 1, wherein the at least one opposed bipolar electrode pair comprises at least two or more opposed bipolar electrode pairs of the plurality of opposed bipolar electrode pairs, the at least two or more opposed bipolar electrode pairs being adjacent to one another, and wherein the compensator module is operable such that it is able to fire the at least two or more opposed bipolar electrode pairs that are adjacent to one another sequentially.

5. The bipolar electrocautery apparatus of claim 1, wherein the compensator module is configured to selectively apply a voltage activating the plurality of opposed bipolar electrode pairs for different firing times for one or more of each of the plurality of opposed bipolar electrode pairs to balance energy supplied by the plurality of opposed bipolar electrode pairs.

6. The bipolar electrocautery apparatus of claim 1, wherein the at least one opposed bipolar electrode pair comprises the plurality of opposed bipolar electrode pairs, and wherein the compensator module is configured to selectively apply a voltage activating the plurality of opposed bipolar electrode pairs in a sequence whereby at least some of the plurality of opposed bipolar electrode pairs fire more frequently than others, and whereby others of the plurality of opposed bipolar electrode pairs do not fire at all.

7. The bipolar electrocautery apparatus of claim 1, wherein the compensator module is configured to fire the plurality of opposed bipolar electrode pairs to prevent local areas of high impedance from impacting overall impedance across the first electrode array.

8. The bipolar electrocautery apparatus of claim 1, wherein the compensator module is configured to energize different ones of the plurality of opposed bipolar electrode pairs to employ unique power and energy delivery profiles for each of the plurality of opposed bipolar electrode pairs based on properties of tissue in a specific electrode location.

9. The bipolar electrocautery apparatus of claim 1, wherein the compensator module is configured to sense and automatically adjust conjugate matching impedance.

10. The bipolar electrocautery apparatus of claim 1, wherein the compensator module is configured to idle the at least one opposed bipolar electrode pair if the compensator module senses that the amount of tissue coverage between the at least one opposed bipolar electrode pair is less than the full amount of tissue coverage.

11. The bipolar electrocautery apparatus of claim 1, wherein the compensator module is configured to provide a warning if the compensator module senses that the amount of tissue coverage between the at least one opposed bipolar electrode pair is less than the full amount of tissue coverage.

12. The bipolar electrocautery apparatus of claim 1, further comprising a status indicator for each of the plurality of opposed bipolar electrode pairs that indicates whether a sealing cycle is active or completed with regard to each of the plurality of opposed bipolar electrode pairs.

13. An electrocautery method, comprising the steps of:
providing a plurality of opposed bipolar electrode pairs comprising a plurality of first electrodes forming a first electrode array and one or more second electrodes;
providing a power supply electrically coupled to at least one opposed bipolar electrode pair of the plurality of opposed bipolar electrode pairs;
detecting, with one or more feedback devices of a compensator module, a voltage, a current, a phase magnitude, and a phase sign of energy supplied to the opposed bipolar electrode pairs by the power supply;
calculating, with a calculation module of the compensator module, a power, a phase, and an impedance based on the voltage, the current, the phase magnitude, and the phase sign in order to sense an amount of tissue coverage between the at least one opposed bipolar electrode pair; and
generating, with a control circuit of the compensator module, a control signal for controlling the energy supplied to the at least one opposed bipolar electrode pair by the power supply based on user-determined set-point information and the calculated power, phase, and impedance from the calculation module, the control signal operable to adjust the impedance by changing a frequency of the energy supplied by the power source across the at least one opposed bipolar electrode pair with the compensator module in response to sensing that the amount of tissue coverage between the at least one opposed bipolar electrode pair is less than a full amount of coverage possible for the at least one opposed bipolar electrode pair.

14. The electrocautery method of claim 13, wherein when, at a beginning of a cauterization cycle, the amount of tissue coverage is sensed to be zero between the at least one opposed bipolar electrode pair, the method further comprises deactivating the at least one opposed bipolar electrode pair.

15. The electrocautery method of claim 13, wherein the at least one opposed bipolar electrode pair comprises at least two of the plurality of opposed bipolar electrode pairs that are adjacent to one another, the electrocautery method further comprising firing the at least two of the plurality of opposed electrode pairs of the plurality of opposed bipolar electrode pairs that are adjacent to one another concurrently.

16. The electrocautery method of claim 13, wherein the at least one opposed bipolar electrode pair comprises at least two of the plurality of opposed bipolar electrode pairs that are adjacent to one another, the electrocautery method further comprising firing the at least two of the plurality of opposed electrode pairs of the plurality of opposed bipolar electrode pairs that are adjacent to one another sequentially.

17. The electrocautery method of claim 13, further comprising selectively applying a voltage activating the plurality of opposed bipolar electrode pairs for different firing times for one or more of each of the plurality of opposed bipolar electrode pairs to balance the energy supplied to the at least one opposed bipolar electrode pair.

18. The electrocautery method of claim 13, wherein the power supply is electrically coupled to the plurality of opposed bipolar electrode pairs, the electrocautery method further comprising selectively applying a voltage activating the plurality of opposed bipolar electrode pairs in a sequence whereby a first subset of the plurality of opposed bipolar electrode pairs fire more frequently than a second subset of the plurality of opposed bipolar electrode pairs, the second subset different from the first subset, and whereby the second subset of the plurality of opposed bipolar electrode pairs comprises one or more opposed bipolar electrode pairs that do not fire at all.

19. The electrocautery method of claim 13, further comprising firing the plurality of opposed bipolar electrode pairs in a manner that prevents local areas of high impedance from impacting overall impedance across the first electrode array.

20. The electrocautery method of claim 13, further comprising energizing different ones of the plurality of opposed bipolar electrode pairs to employ unique power and energy delivery profiles for each of the plurality of opposed bipolar electrode pairs, based on properties of tissue in a specific electrode location.

21. The electrocautery method of claim 13, further comprising sensing and automatically adjusting conjugate matching impedance.

22. The electrocautery method of claim 13, further comprising idling the at least one opposed bipolar electrode pair if the compensator module senses that the amount of tissue coverage between the at least one opposed bipolar electrode pair is less than the full amount of coverage possible.

23. The electrocautery method of claim 13, further comprising providing a warning if the compensator module senses that the at least one opposed bipolar electrode pair is only partially covered by tissue.

24. The electrocautery method of claim 13, further comprising indicating a status for each of the plurality of opposed bipolar electrode pairs as to whether a sealing cycle is active or completed with regard to each of the plurality of opposed bipolar electrode pairs.

* * * * *